(12) United States Patent
Atiya et al.

(10) Patent No.: US 12,310,819 B2
(45) Date of Patent: May 27, 2025

(54) INTRAORAL SCANNER WITH ILLUMINATION SEQUENCING AND CONTROLLED POLARIZATION

(71) Applicant: Align Technology, Inc, San Jose, CA (US)

(72) Inventors: Yossef Y. Atiya, Modiin-Maccabim-Reut (IL); Maayan Moshe, Ramat Hasharon (IL); Ofer Saphier, Rechovot (IL); Shai Ayal, Shoham (IL); Raphael Levy, Jerusalem (IL); Tal Verker, Ofra (IL)

(73) Assignee: Align Technology, Inc., San Jose, CA (US)

( * ) Notice: Subject to any disclaimer, the term of this patent is extended or adjusted under 35 U.S.C. 154(b) by 224 days.

(21) Appl. No.: 17/869,698

(22) Filed: Jul. 20, 2022

(65) Prior Publication Data
US 2023/0025243 A1      Jan. 26, 2023

Related U.S. Application Data

(60) Provisional application No. 63/225,318, filed on Jul. 23, 2021.

(51) Int. Cl.
*A61B 5/00* (2006.01)
*A61B 1/06* (2006.01)
*A61C 9/00* (2006.01)

(52) U.S. Cl.
CPC ............ *A61C 9/006* (2013.01); *A61B 1/0625* (2022.02); *A61B 5/0088* (2013.01)

(58) Field of Classification Search
CPC ..... A61C 9/006; A61C 9/0053; A61B 1/0625; A61B 5/0088; A61B 1/00194; A61B 1/0638; A61B 5/0062; A61B 5/4547
See application file for complete search history.

(56) References Cited

U.S. PATENT DOCUMENTS

| | | |
|---|---|---|
| 6,099,314 A | 8/2000 | Kopelman et al. |
| 6,334,772 B1 | 1/2002 | Taub et al. |
| 6,334,853 B1 | 1/2002 | Kopelman et al. |
| 6,463,344 B1 | 10/2002 | Pavlovskaia et al. |
| 6,542,249 B1 | 4/2003 | Kofman et al. |
| 6,633,789 B1 | 10/2003 | Nikolskiy et al. |
| 6,664,986 B1 | 12/2003 | Kopelman et al. |
| 6,697,164 B1 | 2/2004 | Babayoff et al. |
| 6,845,175 B2 | 1/2005 | Kopelman et al. |
| 6,979,196 B2 | 12/2005 | Nikolskiy et al. |
| 7,030,383 B2 | 4/2006 | Babayoff et al. |
| 7,202,466 B2 | 4/2007 | Babayoff et al. |
| 7,255,558 B2 | 8/2007 | Babayoff et al. |
| 7,286,954 B2 | 10/2007 | Kopelman et al. |
| 7,319,529 B2 | 1/2008 | Babayoff |

(Continued)

*Primary Examiner* — Michelle M Iacoletti
*Assistant Examiner* — Judy Dao Tran
(74) *Attorney, Agent, or Firm* — LOWENSTEIN SANDLER LLP

(57) ABSTRACT

An intraoral scanner includes a probe with a sensing face, patterned light sources that are coupled to the probe, un-patterned light sources coupled to the probe, near infrared (NIR) light sources couple to the probe, cameras coupled to the probe, and a processing device coupled to the probe. The processing device is configured to control an operation of the patterned light sources, the un-patterned light sources, and the NIR light sources.

19 Claims, 13 Drawing Sheets

(56) References Cited

U.S. PATENT DOCUMENTS

| | | |
|---|---|---|
| 7,373,286 B2 | 5/2008 | Nikolskiy et al. |
| 7,507,088 B2 | 3/2009 | Taub et al. |
| 7,545,372 B2 | 6/2009 | Kopelman et al. |
| 7,698,068 B2 | 4/2010 | Babayoff |
| 7,916,911 B2 | 3/2011 | Kaza et al. |
| 8,108,189 B2 | 1/2012 | Chelnokov et al. |
| 8,244,028 B2 | 8/2012 | Kuo et al. |
| 8,587,582 B2 | 11/2013 | Matov et al. |
| 8,948,482 B2 | 2/2015 | Levin |
| D742,518 S | 11/2015 | Barak et al. |
| 9,192,305 B2 | 11/2015 | Levin |
| 9,261,356 B2 | 2/2016 | Lampert et al. |
| 9,261,358 B2 | 2/2016 | Atiya et al. |
| 9,299,192 B2 | 3/2016 | Kopelman |
| D760,901 S | 7/2016 | Barak et al. |
| 9,393,087 B2 | 7/2016 | Moalem |
| 9,408,679 B2 | 8/2016 | Kopelman |
| 9,431,887 B2 | 8/2016 | Boltanski |
| 9,439,568 B2 | 9/2016 | Atiya et al. |
| 9,451,873 B1 | 9/2016 | Kopelman et al. |
| D768,861 S | 10/2016 | Barak et al. |
| D771,817 S | 11/2016 | Barak et al. |
| 9,491,863 B2 | 11/2016 | Boltanski |
| D774,193 S | 12/2016 | Makmel et al. |
| 9,510,757 B2 | 12/2016 | Kopelman et al. |
| 9,660,418 B2 | 5/2017 | Atiya et al. |
| 9,668,829 B2 | 6/2017 | Kopelman |
| 9,675,430 B2 | 6/2017 | Verker et al. |
| 9,693,839 B2 | 7/2017 | Atiya et al. |
| 9,717,402 B2 | 8/2017 | Lampert et al. |
| 9,724,177 B2 | 8/2017 | Levin |
| 9,844,426 B2 | 12/2017 | Atiya et al. |
| 10,076,389 B2 | 9/2018 | Wu et al. |
| 10,098,714 B2 | 10/2018 | Kuo |
| 10,108,269 B2 | 10/2018 | Sabina et al. |
| 10,111,581 B2 | 10/2018 | Makmel |
| 10,111,714 B2 | 10/2018 | Kopelman et al. |
| 10,123,706 B2 | 11/2018 | Elbaz et al. |
| 10,136,972 B2 | 11/2018 | Sabina et al. |
| 10,380,212 B2 | 8/2019 | Elbaz et al. |
| 10,390,913 B2 | 8/2019 | Sabina et al. |
| 10,453,269 B2 | 10/2019 | Furst |
| 10,456,043 B2 | 10/2019 | Atiya et al. |
| 10,499,793 B2 | 12/2019 | Ozerov et al. |
| 10,504,386 B2 | 12/2019 | Levin et al. |
| 10,507,087 B2 | 12/2019 | Elbaz et al. |
| 10,517,482 B2 | 12/2019 | Sato et al. |
| 10,695,150 B2 | 6/2020 | Kopelman et al. |
| 10,708,574 B2 | 7/2020 | Furst et al. |
| 10,772,506 B2 | 9/2020 | Atiya et al. |
| 10,813,727 B2 | 10/2020 | Sabina et al. |
| 10,888,399 B2 | 1/2021 | Kopelman et al. |
| 10,952,816 B2 | 3/2021 | Kopelman |
| 10,980,613 B2 | 4/2021 | Shanjani et al. |
| 11,013,581 B2 | 5/2021 | Sabina et al. |
| D925,739 S | 7/2021 | Shalev et al. |
| 11,096,765 B2 | 8/2021 | Atiya et al. |
| 11,238,586 B2 | 2/2022 | Mikhail et al. |
| 11,367,192 B2 | 6/2022 | Avi et al. |
| 2002/0135752 A1* | 9/2002 | Sokolov ............... A61B 5/444 356/39 |
| 2018/0028064 A1* | 2/2018 | Elbaz ..................... G06T 7/75 |
| 2018/0080828 A1* | 3/2018 | Fink ..................... A61B 1/0625 348/66 |
| 2018/0270474 A1 | 9/2018 | Liu |
| 2019/0029784 A1 | 1/2019 | Moalem et al. |
| 2019/0388193 A1* | 12/2019 | Saphier .................. G06T 7/80 348/66 |
| 2020/0205942 A1* | 7/2020 | Pesach ................. G06V 20/653 |
| 2020/0281702 A1 | 9/2020 | Avi et al. |
| 2020/0315434 A1 | 10/2020 | Kopelman et al. |
| 2020/0349705 A1 | 11/2020 | Minchenkov et al. |
| 2020/0404243 A1 | 12/2020 | Saphier et al. |
| 2021/0030503 A1 | 2/2021 | Shalev et al. |
| 2021/0059796 A1 | 3/2021 | Weiss et al. |
| 2021/0068773 A1 | 3/2021 | Moshe et al. |
| 2021/0121049 A1 | 4/2021 | Rudnitsky et al. |
| 2021/0128281 A1 | 5/2021 | Peleg |
| 2021/0137653 A1 | 5/2021 | Saphier et al. |
| 2021/0196152 A1 | 7/2021 | Saphier et al. |

* cited by examiner

INTRAORAL SCANNER WITH ILLUMINATION SEQUENCING AND CONTROLLED POLARIZATION

RELATED APPLICATIONS

This application claims the benefit of priority to U.S. Provisional Application No. 63/225,318 filed Jul. 23, 2021, the entire contents of which are hereby incorporated in their entirety.

TECHNICAL FIELD

Embodiments of the disclosure generally relate to optical scanners and, in particular, to intraoral three-dimensional imaging.

BACKGROUND

For restorative dental work, one or more intraoral scans may be generated of a preparation tooth and/or surrounding teeth on a patient's dental arch using an intraoral scanner. These intraoral scans are then used to generate a virtual three-dimensional (3D) model of a dental site including the preparation tooth and the surrounding teeth. For example, a virtual 3D model of a patient's dental arch may be generated. The virtual 3D model may then be sent to a lab. Similarly, for orthodontic dental work intraoral scans are generated of one or more dental arches, which are used to generate a virtual 3D model of the one or more dental arches and to generate a treatment plan.

SUMMARY

In a first embodiment, an intraoral scanner comprises: a probe with a sensing face; a plurality of patterned light sources that are coupled to the probe, each of the plurality of patterned light sources configured to emit a pattern of light from a different location of a first plurality of locations with respect to the sensing face of the probe; a plurality of un-patterned light sources coupled to the probe, each of the plurality of un-patterned light sources configured to emit un-patterned light from a different location of a second plurality of locations with respect to the sensing face of the probe; a plurality of near infrared (NIR) light sources couple to the probe, each of the plurality of NIR light sources configured to emit NIR light from a different location of a third plurality of locations with respect to the sensing face of the probe; a plurality of cameras coupled to the probe, each of the plurality of cameras configured to receive one or more of returning patterned light, returning un-patterned light or returning NIR light reflected by a dental site; and a processing device coupled to the probe, the processing device configured to control an operation of the plurality of patterned light sources, the plurality of un-patterned light sources, and the plurality of NIR light sources.

In a second embodiment, the intraoral scanner further comprises: a plurality of polarizing filters coupled to the plurality of cameras, each of the plurality of polarizing filters having a first polarization axis. The first embodiment can extend the first embodiment.

In a third embodiment, each of the plurality of patterned light sources are configured to emit the pattern of light at a second polarization axis, wherein the first polarization axis is substantially parallel to the second polarization axis. The third embodiment can be extended to the first and/or second embodiment.

In a fourth embodiment, each of the plurality of NIR light sources are configured to emit the NIR light at a third polarization axis, wherein the first polarization axis is substantially perpendicular to the third polarization axis. The fourth embodiment can be extended with any of the above embodiments.

In a fifth embodiment, the processing device is configured to operate in an alternating mode to alternately illuminate the dental site by respective light sources within one or more of the plurality of patterned light sources, the plurality of un-patterned light sources, or the plurality of NIR light sources. The fifth embodiment can be extended with any of the above embodiments.

In a sixth embodiments, wherein to operate in the alternating mode to alternately illuminate the dental site, the processing device to: activate one or more first NIR light sources of the plurality of NIR light sources at a first instance in time to emit first NIR light from first location of the third plurality of locations with respect to the sensing face of the probe and to provide a first illumination of the dental site; generate first NIR scan data comprising a first NIR optical image of the dental site based on the first illumination; activate one or more second NIR light sources of the plurality of NIR light sources at a second instance in time to emit second NIR light from second location of the third plurality of locations with respect to the sensing face of the probe and to provide a second illumination of the dental site, wherein at least one of the one or more first NIR light sources are different than at least one of the one or more second NIR light sources; and generate second NIR scan data comprising a second NIR optical image of the dental site based on the second illumination. The sixth embodiment can be extended with any of the above embodiments.

In a seventh embodiment, the first instance in time and the second instance in time are sequential instances in time. The seventh embodiment can be extended with any of the above embodiments.

In an eight embodiment, the processing device further to: generate a blended NIR optical image of the dental site using the first NIR optical image and the second NIR optical image. The eight embodiment can be extended with any of the above embodiments.

In a ninth embodiments, the processing device further to: perform an identification of a carious lesion at the dental site based on one or more of the first NIR optical image, the second NIR optical image, or the blended NIR optical image. The ninth embodiment can be extended with any of the above embodiments.

In the tenth embodiment, the processing device is configured to operate in the alternating mode to alternately illuminate the dental site by respective light sources between two or more of the plurality of patterned light sources, the plurality of un-patterned light sources, or the plurality of NIR light sources. The tenth embodiment can be extended with any of the above embodiments.

In an eleventh embodiment, a method comprises: emitting, at a first instance in time by a first light source of a probe of an intraoral scanner, first light at a first angle with respect to a dental site; detecting, by a first camera of the probe, at least part of the first light reflected from the dental site; emitting, at a second instance in time by a second light source of the probe, second light at a second angle with respect to the dental site; detecting, by the first camera, at least part of the second light reflect from the dental site; and generating a first optical image of the dental site based on the detected first light and a second optical image of the dental site based on the detected second light.

In a twelfth embodiment, the first light source and the second light source are both from one of a plurality of patterned light sources configured to emit a pattern of light, a plurality of un-patterned light sources configured to emit un-patterned light, or a plurality of NIR light sources configured to emit NIR light. The tenth embodiment can be extended with the eleventh embodiment.

In a thirteenth embodiment, the first light source and the second light source are from different ones of a plurality of patterned light sources configured to emit a pattern of light, a plurality of un-patterned light sources configured to emit un-patterned light, or a plurality of near infrared (NIR) light sources configured to emit NIR light. The thirteenth embodiment can be extended with the eleventh and twelfth embodiments.

In a fourteenth embodiment, the first instance in time and the second instance in time are sequential instances in time. The fourteenth embodiment can be extended with any of the above embodiments.

In a fifteenth embodiment, wherein detecting, by the first camera of the probe, the at least part of the first light reflected from the dental site comprises detecting the at least part of the first light reflected from the dental site that is filtered by a polarizing filter having a first polarization axis; and wherein detecting, by the first camera, the at least part of the second light reflect from the dental site comprises detecting the at least part of the second light reflected from the dental site that is filtered by the polarizing filter having a first polarization axis. The fifteenth embodiment can be extended with any of the above embodiments.

In a sixteenth embodiment, each of the first light source and the second light source is a different one of a plurality of patterned light sources and is configured to emit a pattern of light at a second polarization axis, wherein the first polarization axis is substantially parallel to the second polarization axis. The sixteenth embodiment can be extended with any of the above embodiments. The sixteenth embodiment can be extended with any of the above embodiments.

In a seventeenth embodiments, each of the first light source and the second light source is a different one of a plurality of near infrared (NIR) light sources and is configured to emit NIR light at a third polarization axis, wherein the first polarization axis is substantially perpendicular to the third polarization axis. The seventeenth embodiment can be extended with any of the above embodiments.

In the eighteenth embodiment, the method further comprises: generating a blended optical image of the dental site using the first optical image and the second optical image. The eighteenth embodiment can be extended with any of the above embodiments.

In the nineteenth embodiment, the method further comprises: generating a three-dimensional (3D) model of the dental site using one or more of the first optical image, the second optical image, or the blended optical image.

In the twentieth embodiment, the first optical image is a first near infrared (NIR) image, the second optical image is a second NIR image and the blended optical image is a blended NIR image, the method further comprising: performing an identification of a carious lesion at the dental site based on the 3D model of the dental site. The twentieth embodiment can be extended with any of the above embodiments.

In a twenty first embodiment, a method comprises: projecting, by a probe of an intraoral scanner and at a dental site, polarized near infrared (NIR) light at first polarization axis; receiving, by the probe via a camera coupled to a polarization filter having a second polarization axis, at least part of the polarized NIR light reflected from the dental site, wherein the first polarization axis is substantially perpendicular to the second polarization axis; and generating one or more first images of the dental site based on the received polarized NIR light.

In a twenty second embodiments, the method further comprises: projecting, by the probe and at the dental site, a polarized pattern of light at a third polarization axis that is substantially parallel to the second polarization axis associated with the camera; receiving, by the probe via the camera having the polarization filter, at least part of the polarized pattern of light reflected from the dental site; and generating one or more second images of the dental site based on the received polarized pattern of light. The twenty second embodiment can be extended with the twenty first embodiment.

In a twenty third embodiment, the method further comprises: projecting, by the probe and at the dental site, un-patterned light; receiving, by the probe via the camera having the polarization filter, at least part of the un-patterned light reflected from the dental site; and generating one or more third images of the dental site based on the received un-patterned light. The twenty third embodiment can be extended with any of the above embodiments.

In the twenty fourth embodiment, the method further comprises: generating a three-dimensional model of the dental site using the one or more first images of the dental site generated based on the received polarized NIR light, the one or more second images of the dental site generated based on the received polarized pattern of light, and the one or more third images of the dental site generated based on the received un-patterned light. The twenty fourth embodiment can be extended with any of the above embodiments.

In the twenty fifth embodiment, projecting the polarized NIR light at the first polarization axis comprises: emitting, at a first instance in time by a first NIR light source of the probe, first polarized NIR light at a first angle with respect to the dental site; and emitting, at a second instance in time by a second NIR light source of the probe, second polarized NIR light at a second angle with respect to the dental site; wherein receiving the at least part of the polarized NIR light reflected from the dental site comprises: detecting, by the camera having the polarization filter, at least part of the first polarized NIR light reflected from the dental site; and detecting, by the camera having the polarization filter, at least part of the second polarized NIR light reflect from the dental site; and wherein generating the one or more first images of the dental site based on the received polarized NIR light comprises: generating a first optical image of the dental site based on the detected first polarized NIR light and a second optical image of the dental site based on the detected second polarized NIR light. The twenty fifth embodiment can be extended with any of the above embodiments.

In the twenty sixth embodiment, projecting the polarized pattern of light at the third polarization axis that is substantially parallel to the second polarization axis associated with the camera comprises: emitting, at a third instance in time by a first patterned light source of the probe, first polarized pattern of light at a third angle with respect to the dental site; and emitting, at a fourth instance in time by a second patterned light source of the probe, second polarized pattern of light at a fourth angle with respect to the dental site; wherein receiving the at least part of the polarized pattern of light reflected from the dental site comprises: detecting, by the camera having the polarization filter, at least part of the first polarized pattern of light reflected from the dental site; and detecting, by the camera having the polarization filter, at least part of the second polarized pattern of light reflect from the dental site; and wherein generating the one or more second images of the dental site based on the received polarized pattern of light comprises: generating a third optical image of the dental site based on the detected first polarized pattern of light and a fourth optical image of the dental site based on the detected second polarized pattern of light. The twenty sixth embodiment can be extended with any of the above embodiments.

In the twenty seventh embodiment, the first instance in time and the second instance in time are first sequential instances in time. The twenty seventh embodiment can be extended with any of the above embodiments.

In the twenty eighth embodiment, the third instance in time and the fourth instance in time are second sequential instances in time. The twenty eighth embodiment can be extended with any of the above embodiments.

In the twenty ninth embodiment, the first optical image comprises a first NIR optical image and the second optical image comprises a second NIR optical image, the method further comprises: generating a blended NIR optical image of the dental site using the first optical image and the second optical image. The twenty ninth embodiment can be extended with any of the above embodiments.

In the thirtieth embodiment, the method further comprises: performing an identification of a carious lesion at the dental site based on the 3D model. The thirtieth embodiment can be extended with any of the above embodiments.

In a thirty first embodiment a method, comprises: performing any operation as disclosed herein.

In a thirty second embodiment, an apparatus, comprises: one or more of any elements as disclosed herein.

In a thirty third embodiment, a method comprises: performing at least one of alternate illumination or controlled polarization.

A further aspect of the disclosure provides a system comprising: a memory; and a processing device, coupled to the memory, the processing device to perform a method according to any of the first through thirty third embodiments.

A further aspect of the disclosure provides a computer-readable medium comprising instructions that, responsive to execution by a processing device, cause the processing device to perform operations comprising a method according to any first through thirty third embodiments.

A further aspect of the disclosure provides an intraoral scanner comprising a probe and one or more light sources, the intraoral scanner to perform the method of any of the first through thirty third embodiments.

DETAILED DESCRIPTION

Figure 1A:
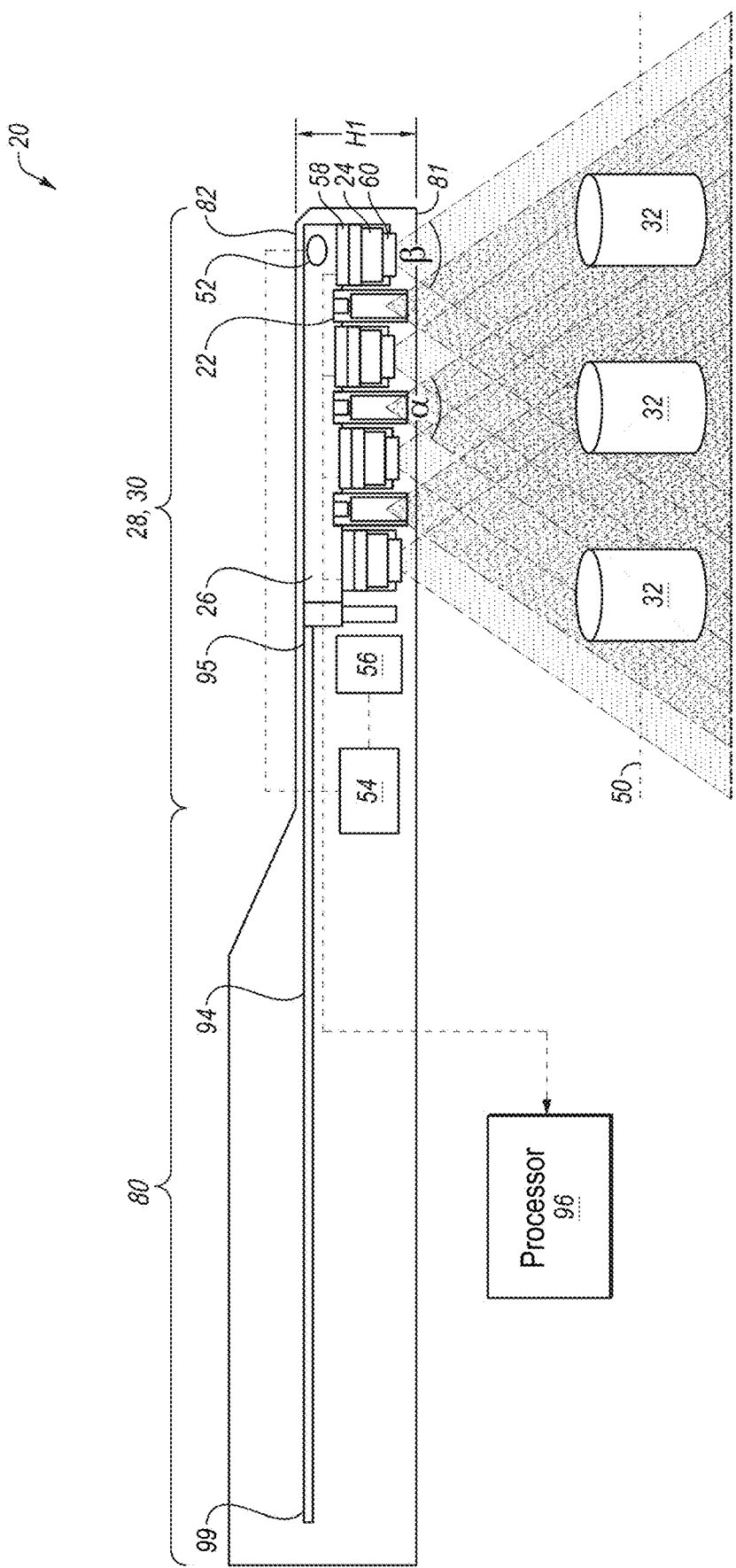
FIG. 1A illustrates a schematic illustration of a wand for an intraoral scanner, in accordance with embodiments of the disclosure.

Described herein is a method and apparatus for improving the quality of scans, such as intraoral scans taken of dental sites for patients. During a scan session, a user (e.g., a dental practitioner) of a scanner may generate multiple different images (also referred to as scans) of a dental site, and model of a dental site, or other object. To generate the multiple different images, the dental site can be illuminated by a particular type of light source. The images may be discrete images (e.g., point-and-shoot images) or frames from a video (e.g., a continuous scan). The images can be registered together and used to generate a three-dimensional (3D) model of the dental site. The 3D model can be used for various purposes including, but not limited to, dental restorations, design of dental prosthetics, design of dental aligners, caries detection, and so forth.

A dental site can be illuminated by different types of light sources. Images generated from each of the different types of light sources can include different information about the dental site. For example, a dental site can be illuminated by un-patterned light sources (also referred to as "uniform light projectors" herein) that emit surface-feature illuminating light (e.g., white light), which can be used to produce color images of surface features of the dental site. The dental site can be illuminated by patterned light sources (also referred to as "structured light projectors" herein) that emit patterned light in a surface-feature illuminating spectral range, which can be used to produce three-dimensional images of surface features of the dental site. The dental site can be illuminated by penetrative light sources (also referred to as "penetrative light projectors" herein) that emit penetrative spectral range light (e.g., infrared or near infrared (NIR)), which can be used to produce images that include information about internal structures or features of the dental site.

Registering images generated using illumination from each type of light source has its own challenges at least because each type of light source interacts with the dental site in a different manner, which can create different types of noise effects that degrade the information content of the respective images. Further, it is desirable to illuminate the dental site with multiple types of light sources during a single intraoral scan in order to collect the different types of information about the dental site. However, using different types of light sources in a single intraoral scan can be challenging at least because of interoperability issues using multiple types of light sources and interference issues illuminating the dental site using the different types of light sources.

Aspects of the disclosure address the above challenges and others by providing an intraoral scanner having one or more types of light sources, including but not limited to, uniform light projectors, structured light projectors, or penetrative light projectors. The one or more different types of light sources can be operated in an illumination sequence that includes alternate illumination, controlled polarization, or combination thereof.

An illumination sequence can refer to a sequence of illuminations (e.g., using illumination source pulses) using one or more of the different types of light sources. Each illumination by a particular type of light source can be used to generate corresponding scan data (e.g., including a corresponding image) of the object (e.g., dental site). Alternate illumination can refer to illuminating an object from different directions (e.g., different illumination angles) and capturing the scan data (e.g., images) from the differently angled illumination with the same camera. Each of the images generated from alternate illumination can have a different quality of information about the same areas of the object, which can be leveraged to generate images having greater quality (e.g., more information) than and single one of the originally obtained images.

For example, a dental site can be illuminate from the left by a first penetrative light projector to generate a left image (e.g., left penetrative image) of the dental site. The dental site can be illuminated from the right immediately following the left illumination by a second penetrative light projector to generate a right image (e.g., right penetrative image) of the dental site. The reflected light from the left illumination and the right illumination can be captured by the same camera. The left image can be saturated on the left area of the dental site but have high contrast on the right side of the dental site. The right image can be saturated on the right area of the dental site but have high contrast on the left side of the dental site. The high contrast image information of the left image and the right image can be combined (e.g., using the high contrast areas of each of the left and right image) to create another image (e.g., blended image) having greater quality of contrast information than any single one of the originally obtained left or right image.

In some embodiments, controlled polarization can be used such that one or more of the different types of light sources can be configured to project respective polarized light at a controlled polarization axis. The cameras can further be configured with polarization filters having a predetermined polarization axis. By implementing controlled polarization for different light sources (and cameras) reflected light that degrades the quality of the image can, at least in part, be reduced and/or filtered.

For example, the penetrative light projectors can be configured to project cross-polarized penetrative light relative to the cameras' polarization axis to help suppress specular reflection from the surface of the dental site. The structured light projectors can be configured to project linear polarized patterned light with respect to the cameras' polarization axis to help suppress patterned light that percolates within the dental site and undergoes multiple scatterings within the tooth before being reflected back to the camera.

In some embodiments, the alternate illumination techniques described herein can be combined with the controlled polarization techniques described herein in a single intraoral scan. In some embodiments, a single intraoral scan can implement one of the alternate illumination techniques or controlled polarization techniques as described herein.

In some embodiments, scan data acquired from one type of light source can be used with scan data acquired from another type of light source in a beneficial manner. For instance, a 3D model of the surface of the dental site can be created using images generated from illumination from structured light projectors. The 3D model of the surface (e.g., geometric data indicative of where the wand was positioned for each respective image) can be used to determine or estimate the position of the wand when corresponding images where taken using illumination from different types of light sources, such as penetrative light projectors or uniform light projectors. Using such information a more complete 3D model, such as a 3D model with surface data, volumetric data and/or color data of the dental site can be created and used for various purposes, such as caries detection.

Embodiments described herein are discussed with reference to intraoral scanners, intraoral images, intraoral scan sessions, and so forth. However, it should be understood that embodiments also apply to types of scanners other than intraoral scanners. Embodiments may apply to any type of scanner that takes multiple optical images and stitches these images together to form a combined image or virtual model. For example, embodiments may apply to desktop model scanners, and so forth. Additionally, it should be understood that the intraoral scanners or other scanners may be used to scan objects other than dental sites in an oral cavity. Accordingly, embodiments describing intraoral images should be understood as being generally applicable to any types of images generated by a scanner that contains optical sensors, embodiments describing intraoral scan sessions should be understood as being applicable to scan sessions for any type of object, and embodiments describing intraoral scanners should be understood as being generally applicable to many types of scanners.

FIG. 1A illustrates a schematic illustration of a wand for an intraoral scanner, in accordance with embodiments of the disclosure. The wand 20 (also referred to as "elongate handheld wand 20" and "intraoral scanner" herein) includes multiple light sources 22 and multiple cameras 24 that are coupled to a rigid structure 26 disposed within a probe 28 at a distal end 30 of the handheld wand. In some applications, during an intraoral scan, probe 28 at least in part enters the oral cavity of a subject.

In some embodiments, the light sources 22 can be of (or operate at) one or more multiple modalities where each modality emits light of a different spectral range and/or different pattern. In some embodiments, the light sources 22 include one or more un-patterned light sources (also referred to as "uniform light projectors" herein) that emit surface-feature illuminating light (e.g., white light or visible light having approximately 400 to 600 nm in wavelength), one or more patterned light sources (also referred to as "structured light projectors" herein) that emit patterned light in a surface-feature illuminating spectral range (e.g., often different than the spectral range of the un-patterned light sources), and/or one or more surface penetrative light sources (also referred to as "penetrative light projectors" herein) that emit penetrative spectral range light (e.g., infrared or near infrared (NIR)). In some embodiments, each modality can capture a particular type of information. For example, uniform light sources that emit surface-feature illuminating light (e.g., white light) can be used to collect scan data that includes color data of the object (e.g., color of the surface of the object). Un-patterned light sources that emit surface-feature illuminating light can be used to collect scan data that includes surface data (e.g., three-dimensional (3D) surface data) of the object. Surface penetrative light sources that emit penetrative light can be used collect scan data that includes penetrative data that includes information about the internal features of the object. For the example, all the different types of light sources can be disposed within a wand 20, as illustrated in FIG. 1C.

In some embodiments, one or more of the light sources 22 can be configured to project polarized light. For example, one or more of the light sources 22 can be configured with linear polarizers to project light in a particular plane (e.g., along a polarization axis). In some embodiments, the light sources 22 can be polarized at the source (e.g., LED configured to emit polarized light). In some embodiments, the light sources 22 can be configured with linear polarizers, such as a polarization filter. In some embodiments, one or more cameras 24 can be configured with linear polarizers. Lights sources 22 with polarizers and cameras 24 with polarizers is further described below with respect to FIG. 1C.

In some embodiments, light sources 22 are positioned within probe 28 such that one or more light sources 22 face an object 32 outside of the handheld wand 20 that is placed in its field of illumination, as opposed to positioning the light source in a proximal end of the handheld wand 20 and illuminating the object 32 by reflection of light off a mirror and subsequently onto the object 32. In some embodiments, cameras 24 are positioned within probe 28 such that one or more cameras 24 face an object 32 outside of the handheld wand 20 that is placed in its field of view, as opposed to positioning the cameras in a proximal end of the handheld wand and viewing the object by reflection of light off a mirror and into the camera. In some embodiments, light sources 22 are positioned within wand 20 such that one or more light sources 22 are positioned in the proximal end 80 of the wand 20 and illuminate the object by reflecting light off one or more mirrors and subsequently onto the object 32. In some embodiments, one or more cameras 24 are positioned in a proximal end of the handheld wand 20 and view the object 32 by reflection of light off one or more mirrors and into the one or more cameras 24.

In some applications, a height H1 of probe 28 is less than 15 mm, height H1 of probe 28 being measured from a lower surface 81 (sensing surface), through which reflected light from object 32 being scanned enters probe 28, to an upper surface 82 opposite lower surface 81. In some applications, the height H1 is between 10-15 mm.

In some embodiments, cameras 24 each have a large field of view β (beta) of at least 45 degrees, e.g., at least 70 degrees, e.g., at least 80 degrees, e.g., 85 degrees. In some embodiments, the field of view may be less than 120 degrees, e.g., less than 100 degrees, e.g., less than 90 degrees. In some embodiments, cameras 24 may include one or more a camera sensor 58, polarizers 60 (e.g., linear polarizers) and objective optics (not shown) including one or more lenses. In some embodiments, to enable close focus imaging cameras 24 may focus at an object focal plane 50 that is located between 1 mm and 30 mm, e.g., between 4 mm and 24 mm, e.g., between 5 mm and 11 mm, e.g., 9 mm-10 mm, from the lens that is farthest from the camera sensor. In some embodiments, cameras 24 may capture images (e.g., scan data) at a frame rate of at least 30 frames per second, e.g., at a frame of at least 75 frames per second, e.g., at least 100 frames per second. In some applications, the frame rate may be less than 200 frames per second. In some embodiments, a large field of view achieved by combining the respective fields of view of all the cameras 24 may improve accuracy due to reduced amount of image (e.g., scan data) stitching errors, especially in edentulous regions, where the gum surface is smooth and there may be fewer clear high resolution 3-D features. In some instances, having a larger field of view enables large smooth features, such as the overall curve of the tooth, to appear in each image frame, which improves the accuracy of stitching respective surfaces obtained from multiple such image frames. The term "field of view" of each of the cameras, as used herein, refers to the diagonal field of view of each of the cameras.

In some embodiments, light sources 22 may each have a large field of illumination α (alpha) of at least 45 degrees, e.g., at least 70 degrees. In some applications, field of illumination α (alpha) may be less than 120 degrees, e.g., than 100 degrees. In some embodiments, each camera 24 has multiple discrete preset focus positions, in each focus position the camera focusing at a respective object focal plane 50. In some embodiments, one or more cameras 24 may include an autofocus actuator that selects a focus position from the discrete preset focus positions in order to improve a given image capture. Additionally or alternatively, one or more cameras 24 includes an optical aperture phase mask that extends a depth of focus of the camera, such that images formed by each camera are maintained focused over all object distances located between 1 mm and 30 mm, e.g., between 4 mm and 24 mm, e.g., between 5 mm and 11 mm, e.g., 9 mm-10 mm, from the lens that is farthest from the camera sensor.

In some embodiments, light sources 22 and cameras 24 are coupled to rigid structure 26 in a closely packed and/or alternating fashion, such that (a) a substantial part of each camera's field of view overlaps the field of view of neighboring cameras, and (b) a substantial part of each camera's field of view overlaps the field of illumination of neighboring projectors. Optionally, at least 20%, e.g., at least 50%, e.g., at least 75% of the projected light are in the field of view of at least one of the cameras at an object focal plane 50 that is located at least 4 mm from the lens that is farthest from the camera sensor.

In some embodiments, rigid structure 26 may be a non-flexible structure to which light sources 22 and cameras 24 are coupled so as to provide structural stability to the optics within probe 28. Coupling all the projectors and all the cameras to a common rigid structure can help maintain geometric integrity of the optics of each structured light projector and each camera 24 under varying ambient conditions, e.g., under mechanical stress as may be induced by the subject's mouth. In some embodiments, rigid structure 26 can help maintain stable structural integrity and positioning of light sources 22 and cameras 24 with respect to each other. In some embodiments, controlling the temperature of rigid structure 26 may help enable maintaining geometrical integrity of the optics through a large range of ambient temperatures as probe 28 enters and exits a subject's oral cavity or as the subject breathes during a scan.

In some embodiments, at least one temperature sensor 52 is coupled to rigid structure 26 and measures a temperature of rigid structure 26. Temperature control circuitry 54 disposed within handheld wand 20 (a) receives data from temperature sensor 52 indicative of the temperature of rigid structure 26 and (b) activates a temperature control unit 56 in response to the received data. Temperature control unit 56, e.g., a PID controller, keeps probe 28 at a desired temperature (e.g., between 35 and 43 degrees Celsius, between 37 and 41 degrees Celsius, etc.).

In some embodiments, probe 28 is maintained at its controlled temperature through the use of a combination of heating and cooling. For example, temperature control unit 56 may include a heater, e.g., a plurality of heaters, and a cooler, e.g., a thermoelectric cooler. If the temperature of probe 28 drops below 38 degrees Celsius the heater(s) may be used to raise the temperature of probe 28, and if the temperature of probe 28 goes above 40 degrees Celsius, the thermoelectric cooler may be used to lower the temperature of probe 28.

In some embodiments, external environmental temperatures, such as those encountered within a subject's intraoral cavity, may however cause heating of probe 28. To overcome this, heat may be drawn out of the probe 28 via a heat conducting element 94, e.g., a heat pipe, that is disposed within handheld wand 20, such that a distal end 95 of heat conducting element 94 is in contact with rigid structure 26 and a proximal end 99 is in contact with a proximal end 80 of handheld wand 20. Heat is thereby transferred from rigid structure 26 to proximal end 80 of handheld wand 20. Alternatively or additionally, a fan disposed in a handle region of handheld wand 20 may be used to draw heat out of probe 28.

In some embodiments, light sources 22 include one or more uniform light projectors coupled to rigid structure 26. In some embodiments, a uniform light projector emits white light (e.g., un-patterned light) onto object 32 being scanned. At least one camera, e.g., one of the cameras 24, captures two-dimensional (2D) color images (e.g., 2D scan data) of object 32 using illumination from uniform light projector. In some embodiments, processor 96 (also referred to as "processing device 96" herein) may run a surface reconstruction algorithm that combines at least one image captured using illumination from other light sources 22 (e.g., structured light sources) with one or more images captured using illumination from uniform light projector in order to generate a digital three-dimensional image of the intraoral three-dimensional surface. In some embodiments, using a combination of structured light and uniform illumination can enhances the overall capture of the intraoral scanner and may help reduce the number of options that processor 96 needs to consider when running a correspondence algorithm.

In some embodiments, light sources 22 can include one or more structured light projectors, as described further below with respect to FIG. 1B. In some embodiments, a structured light projector may project a pattern of light onto object 32 being scanned. For example, the structured light projector may project a blue light pattern at a wavelength of 420-470 nm. At least one of the cameras 24 can capture a light field resulting from the light pattern reflecting off object 32 being scanned. In some embodiments, one or more uniform light projectors transmit white light onto object 32 and one or more cameras 24 capture one or more 2-dimensional (2D) scan data (e.g., 2D color images) of object 32 under the white light illumination. Processor 96 may combine (a) information captured from the patterned light field with (b) at least one 2-dimensional scan data of object 32 to reconstruct a 3-dimensional scan data (e.g., image) of the surface of object 32.

In some embodiments, light sources 22 can in include one or more surface penetrative light sources that emit penetrative spectral range light (e.g., infrared or near infrared (NIR). Penetrative light sources can use penetrative illumination to acquire penetrative scan data (e.g., a penetration image). Penetrative illumination is generally penetrative, so that it may at least partially penetrate and pass through the enamel and dentin of the teeth. Penetrative wavelengths of light may include generally infrared (and particularly near infrared) light. For example, light in the range of 700 to 1090 nm (e.g., 850 nm) may be used. Other wavelengths and ranges of wavelengths may be used, including wavelengths shorter or outside the visible spectrum, such as ultraviolet (UV)/Blue fluorescence and red light fluorescence.

In some embodiments, the illumination used to take a penetration image can be considered semi-penetrative in the sense that internal tooth regions (e.g., points or voxels) may be visible from only a few camera positions and orientations. The point may be obstructed by other structures in some images which include the volume point in their field of view. Images that include the volume point in their field of view may not image this volume point.

In some embodiments, each camera includes a camera sensor that has an array of pixels, for each of which there exists a corresponding ray in 3-D space originating from the pixel whose direction is towards an object being imaged; each point along a particular one of these rays, when imaged on the sensor, will fall on its corresponding respective pixel on the sensor. As used throughout this application, the term used for this is a "camera ray." Similarly, for each projected spot from each projector there exists a corresponding projector ray. Each projector ray corresponds to a respective path of pixels on at least one of the camera sensors, i.e., if a camera sees a spot projected by a specific projector ray, that spot will necessarily be detected by a pixel on the specific path of pixels that corresponds to that specific projector ray. Values for (a) the camera ray corresponding to each pixel on the camera sensor of each of the cameras, and (b) the projector ray corresponding to each of the projected spots of light from each of the projectors, may be stored during a calibration process.

In some embodiments, based on the stored calibration values a processing device may be used to run a correspondence algorithm in order to identify a three-dimensional location for each projected spot on the surface. For a given projector ray, the processing device "looks" at the corresponding camera sensor path on one of the cameras. Each detected spot along that camera sensor path will have a camera ray that intersects the given projector ray. That intersection defines a three-dimensional point in space. The processor then searches among the camera sensor paths that correspond to that given projector ray on the other cameras and identifies how many other cameras, on their respective camera sensor paths corresponding to the given projector ray, also detected a spot whose camera ray intersects with that three-dimensional point in space. As used herein throughout the present application, if two or more cameras detect spots whose respective camera rays intersect a given projector ray at the same three-dimensional point in space, the cameras are considered to "agree" on the spot being located at that three-dimensional point. Accordingly, the processing device may identify three-dimensional locations of the projected light (e.g., projected) pattern of light) based on agreements of the two or more cameras on there being the projected pattern of light by projector rays at certain intersections. The process is repeated for the additional spots along a camera sensor path, and the spot for which the highest number of cameras "agree" is identified as the spot that is being projected onto the surface from the given projector ray. A three-dimensional position on the surface is thus computed for that spot.

In some embodiments, once a position on the surface is determined for a specific spot, the projector ray that projected that spot, as well as all camera rays corresponding to that spot, may be removed from consideration and the correspondence algorithm may be run again for a next projector ray. Ultimately, the identified three-dimensional locations may be used to generate a digital three-dimensional model of the intraoral surface.

Figure 1B:
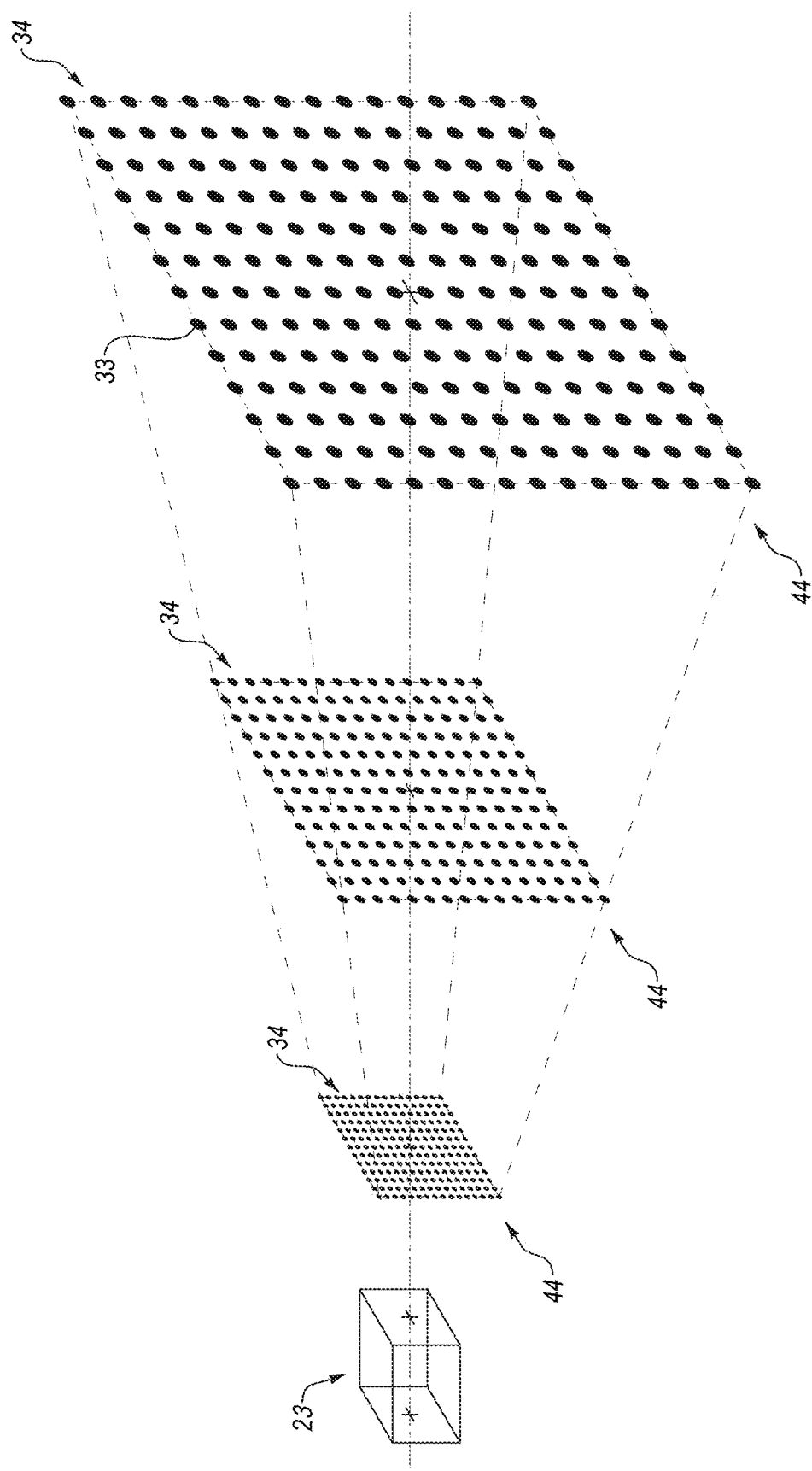
FIG. 1B illustrates a structured light projector, in accordance with some embodiments of the disclosure.
Figure 1C:
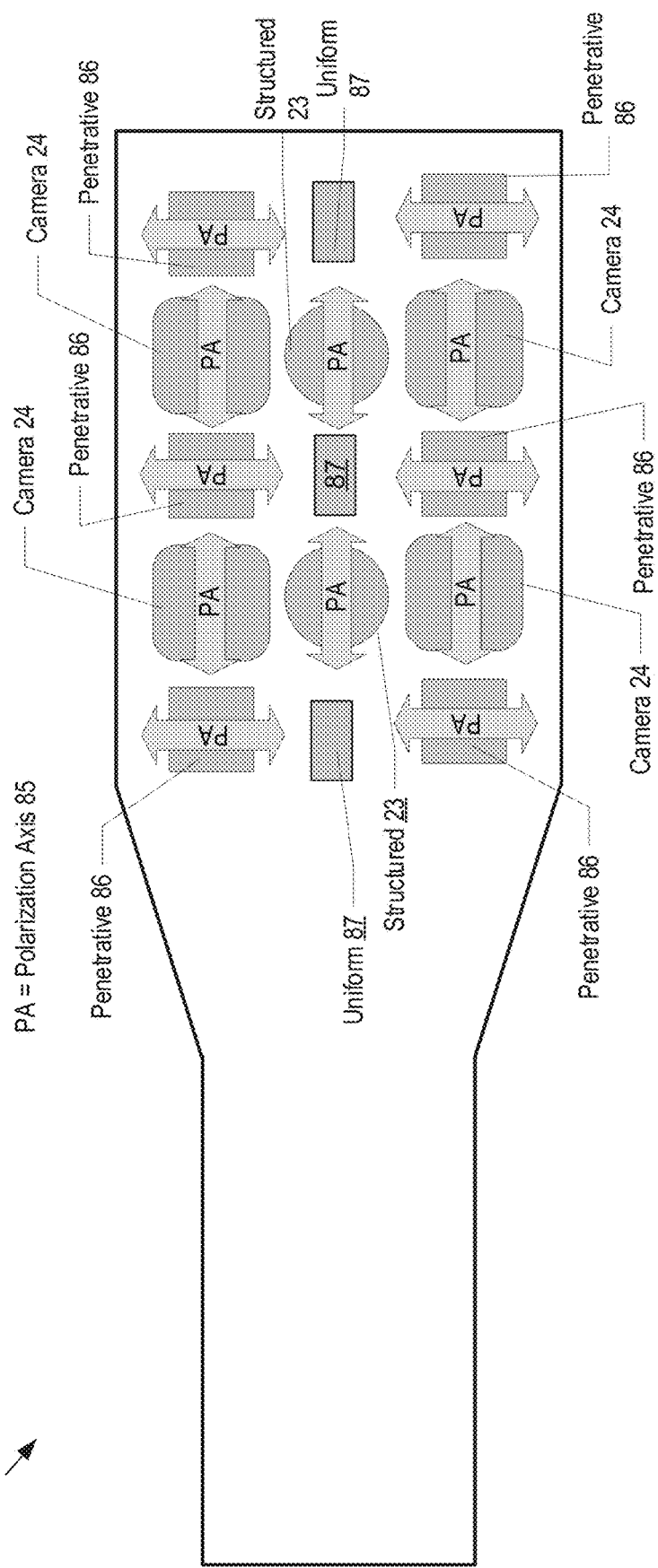
FIG. 1C illustrates the probe of the wand with multiple light sources, multiple cameras, and respective polarization axes, in accordance with embodiments of the disclosure.

FIG. 1B illustrates a structured light projector, in accordance with some embodiments of the disclosure. In some embodiments, light sources 22 can include one or more structured light projectors coupled to rigid structure 26. In some embodiments, a structured light projector 23 can include one or more of a laser diode, a beam shaping optical element, or a pattern generating optical element that generates a pattern of light (e.g. light projected with illuminated and non-illuminated areas), such as a distribution 34 of discrete unconnected spots of light. In some embodiments, the structured light projector 23 may be configured to generate a distribution 34 of discrete unconnected spots of light at all planes located between 1 mm and 30 mm, e.g., between 4 mm and 24 mm, from pattern generating optical element when the laser diode transmits light through pattern generating optical element. While described above as using laser diodes, it should be understood that this is an exemplary and non-limiting application. Other light sources may be used in other applications. Further, while described as projecting a pattern of discrete unconnected spots of light, it should be understood that this is an exemplary and non-limiting application. Other patterns or arrays of lights may be used in other applications, including but not limited to, lines, grids, checkerboards, and other arrays.

In some embodiments, respective laser diodes of respective structured light projectors 23 transmit light at different wavelengths, i.e., respective laser diodes of at least two structured light projectors 23 transmit light at two distinct wavelengths, respectively. In some embodiments, respective laser diodes of at least three structured light projectors 23 transmit light at three distinct wavelengths, respectively. For example, red, blue, and green laser diodes may be used. For some applications, respective laser diodes of at least two structured light projectors 23 transmit light at two distinct wavelengths, respectively. For example, in some applications there are six structured light projectors 23 disposed within probe 28, three of which contain blue laser diodes and three of which contain green laser diodes.

In some embodiments, at least one of the structured light projectors 23 may be a monochrome structured light projector that projects a monochrome structured light pattern onto object being scanned. For example, the monochrome structured light projector may project a blue structured light pattern at a wavelength of 420-470 nm. In some embodiments, at least one of the light field cameras may be a monochrome light field camera that captures a light field resulting from the monochrome structured light pattern reflecting off object being scanned.

As illustrated, structured light projector 23 can project a distribution of discrete unconnected spots of light onto a plurality of object focal planes. In some embodiments, object 32 being scanned may be one or more teeth or other intraoral object/tissue inside a subject's mouth. The somewhat translucent and glossy properties of teeth may affect the contrast of the structured light pattern being projected. For example, (a) some of the light hitting the teeth may scatter to other regions within the intraoral scene, causing an amount of stray light, and (b) some of the light may penetrate the tooth and subsequently come out of the tooth at any other point. A sparse distribution 34 of patterned light (e.g., distribution of discrete unconnected spots of light) may provide an improved balance between reducing the amount of projected light while maintaining a useful amount of information. The sparseness of distribution 34 may be characterized by a ratio of: (a) illuminated area on an orthogonal plane 44 in field of illumination α (alpha), i.e., the sum of the area of all projected spots 33 on the orthogonal plane 44 in field of illumination α (alpha), to (b) non-illuminated area on orthogonal plane 44 in field of illumination α (alpha). In some applications, sparseness ratio may be at least 1:150 and/or less than 1:16 (e.g., at least 1:64 and/or less than 1:36).

In some embodiments, pattern generating optical element is a diffractive optical element (DOE) that generates distribution 34 of discrete unconnected spots 33 of light when laser diode transmits light through DOE onto object 32. A spot of light can refer to a small area of light having any shape. In some embodiments, respective DOE's of different structured light projectors 23 generate spots having different respective shapes, i.e., every spot 33 generated by a specific DOE has the same shape, and the shape of spots 33 generated by at least one DOE is different from the shape of spots 33 generated by at least one other DOE. By way of example, some of DOE's may generate circular spots 33, some of DOE's may generate square spots, and some of the DOE's may generate elliptical spots. Optionally, some DOE's may generate line patterns, connected or unconnected.

In some embodiments, generating a digital three-dimensional model of an intraoral surface may include projecting a pattern of discrete unconnected spots onto an intraoral surface of a patient using one or more structured light projectors disposed in a probe at a distal end of an intraoral scanner. In some embodiments, the pattern of discrete unconnected spots is non-coded. In some embodiments, scan data including multiple images is captured of the projected pattern of unconnected spots using two or more cameras disposed in the probe. The scan data (e.g., the images of the projected pattern) is decoded to determine three-dimensional surface information of the intraoral surface. The three-dimensional surface information can be used to generate a digital three-dimensional model of the intraoral surface. In some embodiments, decoding the scan data (e.g., images) may include accessing calibration data that associates camera rays corresponding to pixels on a camera sensor of each of the two or more cameras to projector rays. Each of the projector rays is associated with one of the discrete unconnected spots. The decoding may further include determining intersections of projector rays and camera rays corresponding to the projected pattern of discrete unconnected spots using the calibration data. The intersections of the projector rays and the camera rays are associated with three-dimensional points in space. The decoding may further include identifying three-dimensional locations of the projected pattern of discrete unconnected spots based on agreements of the two or more cameras on there being the projected pattern of discrete unconnected spots by projector rays at certain intersections.

FIG. 1C illustrates the probe of the wand with multiple light sources, multiple cameras, and respective polarization axes, in accordance with embodiments of the disclosure. Probe 28 is illustrated with light sources 22 that include multiple uniform light projectors 87, multiple structured light projectors 23, multiple penetrative light projectors 86, and multiple cameras 24 arranged at the probe 28. In some embodiments, and as illustrated, various light sources 22 can emit respective light along a particular polarization axis 85. In some embodiments, the polarization axes 85 of the various light sources 22 and camera are arranged with respect to one another in beneficial arrangement. As noted above, the light sources 22 and/or cameras 24 can be polarized at the sources (e.g., respective LED) or using polarization filters, such as linear polarizers or cross-polarizers.

In some embodiments, one or more cameras 24 can be configured with linear polarizers (with respect to a light source, such as structured light projectors) that help the cameras 24 reject irrelevant scattered light. In some embodiments, the polarization axes 85 of one or more cameras 24 can be substantially aligned (e.g., substantially parallel) with the polarization axes 85 of one or more structured light projectors 23. In some embodiments, the polarization axes 85 of one or more (or at least two) cameras 24 can be substantially aligned (e.g., substantially parallel) with the polarization axes 85 of at least two structured light projectors 23. In some embodiments, substantially parallel can refer to within the manufacturing tolerance of absolute parallel, ±3 degrees from parallel, ±5 degrees from parallel, or ±10 degrees from parallel. In some embodiments, substantially parallel is less than 45 degrees from parallel. It can be noted that as the polarization axes 85 of the cameras 24 and structured light projectors 23 move away from absolute parallel the filtering benefits tend to decrease, yet the arrangement can still be effective in rejecting at least some scattered light.

In some embodiments, using polarization axes 85 of cameras 24 that are substantially parallel to the polarization axes 85 of one or more structured light projectors 23 can help with the suppression of diffused and/or percolated light from the object. The suppression of diffused and/or percolated light can improve the peak to background (PTB) ratio for weak spots and allows for a reduction of the threshold in pattern finding, which can increase the contrast per image (e.g., scene). For example, in some three-dimensional imaging systems, a haze around the pattern of light that is projected on the object can result in low PTB (or low signal to noise ratio (SNR)) for weak spots (e.g., pattern), which can be challenging for spot detection. The haze (e.g., background noise) can include light that percolates into the object (e.g., tooth) and undergoes multiple scatterings within the object. The PTB dynamic range is large since the spot peak from surface reflections changes significantly with the acceptance angle while the haze from multiple internal scatterings depends loosely on the acceptance angle (e.g., remains materially unchanged with different acceptance angles). The polarization scheme with respect to structured light projectors 23 can help reduce the PTB component from percolation because the surface reflections help preserve polarization while the haze does not preserve polarization due to multiple scatterings.

In some embodiments, the polarization axes 85 of one or more cameras 24 can be substantially perpendicular with the polarization axes 85 of one or more penetrative light projectors 86 (e.g., cross-polarization). In some embodiments, the polarization axes 85 of one or more (or at least two) cameras 24 can be substantially perpendicular with the polarization axes 85 of at least two penetrative light projectors 86. In some embodiments, one or more penetrative light projectors 86 can be configured with cross polarizers such that the polarization axes 85 of one or more cameras 24 are substantially perpendicular with the polarization axes 85 of one or more penetrative light projectors 86. Configuring the polarization axes 85 of one or more cameras 24 substantially perpendicular to the polarization axes 85 of one or more penetrative light projectors 86 helps suppress reflection, such as specular reflection, of the surface of the object. In some embodiments, substantially perpendicular can refer to within the manufacturing tolerance of absolute perpendicular, ±3 degrees from perpendicular, ±5 degrees from perpendicular, or ±10 degrees from perpendicular. In some embodiments, substantially perpendicular is less than 45 degrees from perpendicular. If can be noted that as the polarization axes 85 of the cameras 24 and penetrative light projectors 86 move away from absolute perpendicular the filtering benefits tend to decrease, yet the arrangement can still be effective in the suppression of at least some reflected light.

In some embodiments using cross polarization with respect to the cameras 24 and the penetrative light projectors 86 can help suppress specular reflection of the penetrative light and enhance the contrast. Illuminating and object with penetrative light projectors 86 creates specular reflections coming from the object. The specular reflections can produce localized saturations at the image sensor of the camera 24, which obstructs the signal representing the internal portions of the object and decrease the image quality. Specular reflection suppression can be enabled using cross-polarizers with respect to the cameras' 24 polarization axes 85. Specular reflections off the object can be suppressed with the polarization scheme used with penetrative light projectors 86 because the specular reflections off the object surface can be suppressed since such specular reflection preserve polarization on reflection while light percolating through the object is scattered back with primarily random polarization. Roughly 50% of the oriented polarized light is transmitted by the camera polarizer and roughly 50% cross polarization is blocked by the camera polarizer such that roughly 25% of the original penetrative light is received by the cameras (most of which is light scattered internal to the teeth).

In some embodiments, one or more of the uniform light projectors 87 can be configured without a polarizer (e.g., such that the uniform light projectors 87 emit randomly polarized light). In some embodiments, one or more of the uniform light projectors 87 can be configured with linear polarizers. The polarization axes 85 of one or more cameras 24 can be substantially aligned (e.g., substantially parallel) with the polarization axes 85 of one or more uniform light projectors 87 configured with linear polarizers. In some embodiments, one or more uniform light projectors 87 can be configured with cross-polarizers such that the polarization axes 85 of one or more cameras 24 are substantially perpendicular with the polarization axes 85 of one or more uniform light projectors 87.

Figure 1D:
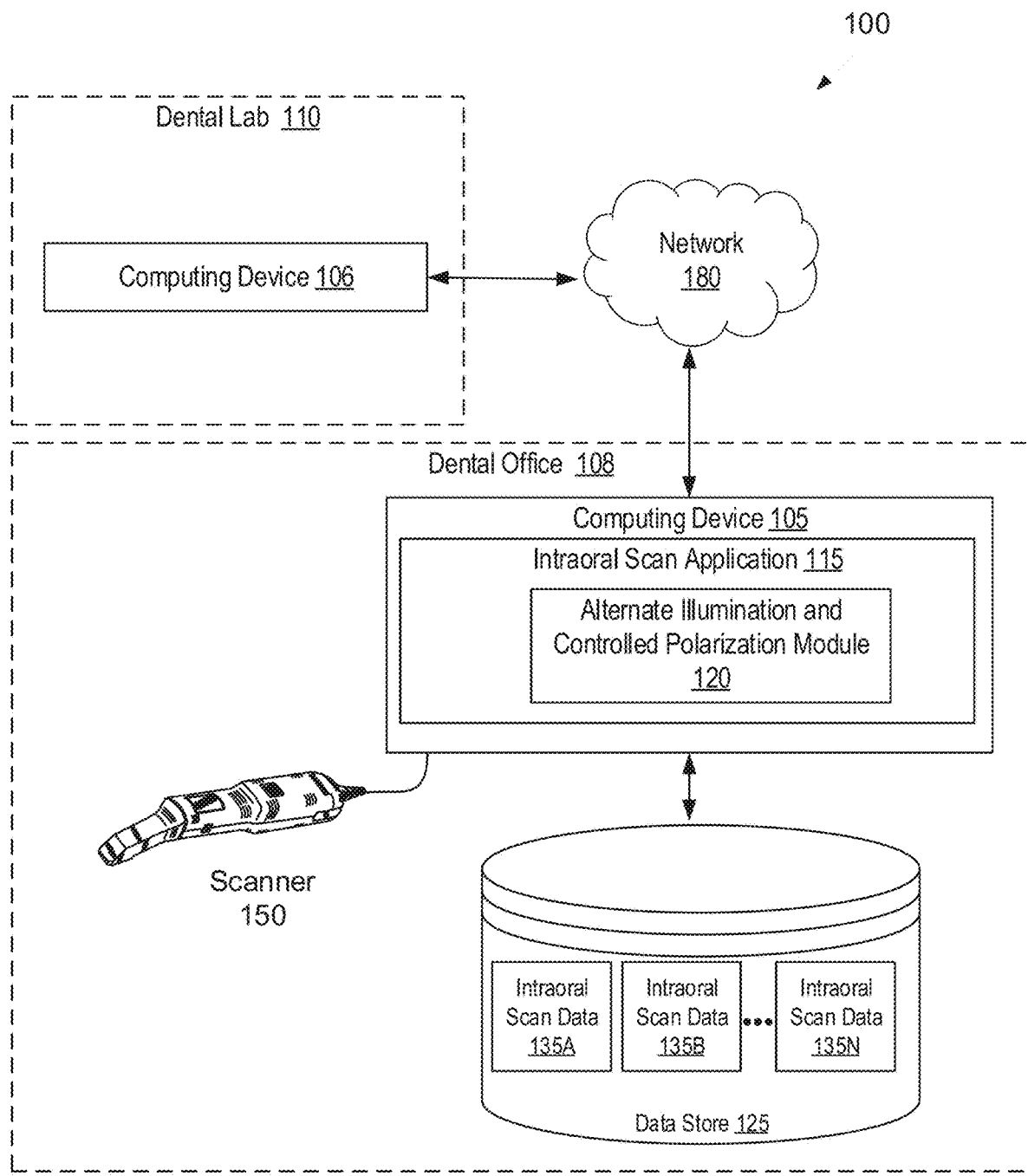
FIG. 1D illustrates one embodiment of a system for performing intraoral scanning and/or generating a virtual three-dimensional model of an intraoral site, in accordance with embodiments of the disclosure.

FIG. 1D illustrates one embodiment of a system 100 for performing intraoral scanning and/or generating a virtual three-dimensional model of an intraoral site, in accordance with embodiments of the disclosure. System 100 includes a dental office 108 and optionally one or more dental lab 110. The dental office 108 and the dental lab 110 each include a computing device 105, 106, where the computing devices 105, 106 may be connected to one another via a network 180. The network 180 may be a local area network (LAN), a public wide area network (WAN) (e.g., the Internet), a private WAN (e.g., an intranet), or a combination thereof.

Computing device 105 may be coupled to one or more intraoral scanner 150 (also referred to as a "scanner" or "wand" herein) and/or a data store 125 via a wired or wireless connection. In one embodiment, multiple scanners 150 in dental office 108 wirelessly connect to computing device 105. In one embodiment, scanner 150 is wirelessly connected to computing device 105 via a direct wireless connection. In one embodiment, scanner 150 is wirelessly connected to computing device 105 via a wireless network. In one embodiment, the wireless network is a Wi-Fi network. In one embodiment, the wireless network is a Bluetooth network, a Zigbee network, or some other wireless network. In one embodiment, the wireless network is a wireless mesh network, examples of which include a Wi-Fi mesh network, a Zigbee mesh network, and so on. In an example, computing device 105 may be physically connected to one or more wireless access points and/or wireless routers (e.g., Wi-Fi access points/routers). Intraoral scanner 150 may include a wireless module such as a Wi-Fi module, and via the wireless module may join the wireless network via the wireless access point/router. Computing device 106 may also be connected to a data store (not shown). The data stores may be local data stores and/or remote data stores. Computing device 105 and computing device 106 may each include one or more processing devices, memory, secondary storage, one or more input devices (e.g., such as a keyboard, mouse, tablet, touchscreen, microphone, camera, and so on), one or more output devices (e.g., a display, printer, touchscreen, speakers, etc.), and/or other hardware components.

In embodiments, scanner 150 includes an inertial measurement unit (IMU). The IMU may include an accelerometer, a gyroscope, a magnetometer, a pressure sensor and/or other sensor. For example, scanner 150 may include one or more micro-electromechanical system (MEMS) IMU. The IMU may generate inertial measurement data, including acceleration data, rotation data, and so on.

Computing device 105 and/or data store 125 may be located at dental office 108 (as shown), at dental lab 110, or at one or more other locations such as a server farm that provides a cloud computing service. Computing device 105 and/or data store 125 may connect to components that are at a same or a different location from computing device 105 (e.g., components at a second location that is remote from the dental office 108, such as a server farm that provides a cloud computing service). For example, computing device 105 may be connected to a remove server, where some operations of intraoral scan application 115 (e.g., alternate illumination and controlled polarization module 120) are performed on computing device 105 (alternate illumination and controlled polarization module 120) and some operations of intraoral scan application 115 are performed on the remote server. It can further be noted that one or more operations described as being performed by intraoral scan application 115 can be performed by alternate illumination and controlled polarization module 120.

Some additional computing devices may be physically connected to the computing device 105 via a wired connection. Some additional computing devices may be wirelessly connected to computing device 105 via a wireless connection, which may be a direct wireless connection or a wireless connection via a wireless network. In embodiments, one or more additional computing devices may be mobile computing devices such as laptops, notebook computers, tablet computers, mobile phones, portable game consoles, and so on. In embodiments, one or more additional computing devices may be traditionally stationary computing devices, such as desktop computers, set top boxes, game consoles, and so on. The additional computing devices may act as thin clients to the computing device 105. In one embodiment, the additional computing devices access computing device 105 using remote desktop protocol (RDP). In one embodiment, the additional computing devices access computing device 105 using virtual network control (VNC). Some additional computing devices may be passive clients that do not have control over computing device 105 and that receive a visualization of a user interface of intraoral scan application 115. In one embodiment, one or more additional computing devices may operate in a master mode and computing device 105 may operate in a slave mode.

Intraoral scanner 150 may include a probe (e.g., also referred to as a hand held probe) for optically capturing three-dimensional structures. The intraoral scanner 150 may be used to perform an intraoral scan of a patient's oral cavity. An intraoral scan application 115 running on computing device 105 may communicate with the scanner 150 to effectuate the intraoral scan. A result of the intraoral scan may be intraoral scan data 135A, 135B through 135N that may include one or more sets of intraoral scans, which may include intraoral images. Each intraoral scan may include a two-dimensional (2D) or 3D image that may include depth information (e.g., a height map) of a portion of a dental site. In embodiments, intraoral scans include x, y and z information. In one embodiment, the intraoral scanner 150 generates numerous discrete (i.e., individual) intraoral scans.

In some embodiments, sets of discrete intraoral scans are merged into a smaller set of blended intraoral scans, where each blended scan is a combination of multiple discrete scans. The intraoral scan data 135A-N may include raw scans and/or blended scans, each of which may be referred to as intraoral scans (and in some instances as intraoral images). While scanning, the intraoral scanner may generate multiple (e.g., tens) of scans (e.g., height maps) per second (referred to as raw scans). In order to improve the quality of the data captured, a blending process may be used to combine a sequence of raw scans into a blended scan by some averaging process. Additionally, intraoral scanner 150 may generate many scans per second. This may be too much data to process using a machine learning model in real time. Accordingly, groups of similar scans may be combined into the blended scans, and the blended scans may be input into one or more trained machine learning model. This may vastly reduce the computation resources used to process the intraoral scans without degrading quality. In one embodiment, each blended scan includes data from up to 20 raw scans, and further includes scans that differ by less than a threshold angular difference from one another and/or by less than a threshold positional difference from one another. Accordingly, some blended scans may include data from 20 scans, while other blended scans may include data from fewer than 20 scans. In one embodiment, the intraoral scan (which may be a blended scan) includes height values and intensity values for each pixel in the image.

Intraoral scan data 135A-N may also include color 2D images and/or images of particular wavelengths (e.g., near-infrared (NIRI) images, infrared images, ultraviolet images, etc.) of a dental site in embodiments. In embodiments, intraoral scanner 150 alternates between generation of 3D intraoral scans and one or more types of 2D intraoral images (e.g., color images, NIRI images, etc.) during scanning. For example, one or more 2D color images may be generated between generation of a fourth and fifth intraoral scan. For example, some scanners may include multiple image sensors that generate different 2D color images of different regions of a patient's dental arch concurrently. These 2D color images may be stitched together to form a single color representation of a larger field of view that includes a combination of the fields of view of the multiple image sensors.

The scanner 150 may transmit the intraoral scan data 135A, 135B through 135N to the computing device 105.

Computing device 105 may store the intraoral scan data 135A-135N in data store 125.

According to an example, a user (e.g., a practitioner) may subject a patient to intraoral scanning. In doing so, the user may apply scanner 150 to one or more patient intraoral locations. The scanning may be divided into one or more segments (also referred to as roles). As an example, the segments may include a lower dental arch of the patient, an upper dental arch of the patient, one or more preparation teeth of the patient (e.g., teeth of the patient to which a dental device such as a crown or other dental prosthetic will be applied), one or more teeth which are contacts of preparation teeth (e.g., teeth not themselves subject to a dental device but which are located next to one or more such teeth or which interface with one or more such teeth upon mouth closure), and/or patient bite (e.g., scanning performed with closure of the patient's mouth with the scan being directed towards an interface area of the patient's upper and lower teeth). Via such scanner application, the scanner 150 may provide intraoral scan data 135A-N to computing device 105. The intraoral scan data 135A-N may be provided in the form of intraoral scan data sets, each of which may include 2D intraoral images (e.g., color 2D images) and/or 3D intraoral scans of particular teeth and/or regions of an intraoral site. In one embodiment, separate intraoral scan data sets are created for the maxillary arch, for the mandibular arch, for a patient bite, and/or for each preparation tooth. Alternatively, a single large intraoral scan data set is generated (e.g., for a mandibular and/or maxillary arch). Intraoral scans may be provided from the scanner 150 to the computing device 105 in the form of one or more points (e.g., one or more pixels and/or groups of pixels). For instance, the scanner 150 may provide an intraoral scan as one or more point clouds. The intraoral scans may each comprise height information (e.g., a height map that indicates a depth for each pixel).

The manner in which the oral cavity of a patient is to be scanned may depend on the procedure to be applied thereto. For example, if an upper or lower denture is to be created, then a full scan of the mandibular or maxillary edentulous arches may be performed. In contrast, if a bridge is to be created, then just a portion of a total arch may be scanned which includes an edentulous region, the neighboring preparation teeth (e.g., abutment teeth) and the opposing arch and dentition. Alternatively, full scans of upper and/or lower dental arches may be performed if a bridge is to be created.

By way of non-limiting example, dental procedures may be broadly divided into prosthodontic (restorative) and orthodontic procedures, and then further subdivided into specific forms of these procedures. Additionally, dental procedures may include identification and treatment of gum disease, sleep apnea, and intraoral conditions. The term prosthodontic procedure refers, inter alia, to any procedure involving the oral cavity and directed to the design, manufacture or installation of a dental prosthesis at a dental site within the oral cavity (intraoral site), or a real or virtual model thereof, or directed to the design and preparation of the intraoral site to receive such a prosthesis. A prosthesis may include any restoration such as crowns, veneers, inlays, onlays, implants and bridges, for example, and any other artificial partial or complete denture. The term orthodontic procedure refers, inter alia, to any procedure involving the oral cavity and directed to the design, manufacture or installation of orthodontic elements at an intraoral site within the oral cavity, or a real or virtual model thereof, or directed to the design and preparation of the intraoral site to receive such orthodontic elements. These elements may be appliances including but not limited to brackets and wires, retainers, clear aligners, or functional appliances.

In embodiments, intraoral scanning may be performed on a patient's oral cavity during a visitation of dental office 108. The intraoral scanning may be performed, for example, as part of a semi-annual or annual dental health checkup. The intraoral scanning may also be performed before, during and/or after one or more dental treatments, such as orthodontic treatment and/or prosthodontic treatment. The intraoral scanning may be a full or partial scan of the upper and/or lower dental arches, and may be performed in order to gather information for performing dental diagnostics, to generate a treatment plan, to determine progress of a treatment plan, and/or for other purposes. The dental information (intraoral scan data 135A-N) generated from the intraoral scanning may include 3D scan data, 2D color images, NIRI and/or infrared images, and/or ultraviolet images, of all or a portion of the upper jaw and/or lower jaw. The intraoral scan data 135A-N may further include one or more intraoral scans showing a relationship of the upper dental arch to the lower dental arch. These intraoral scans may be usable to determine a patient bite and/or to determine occlusal contact information for the patient. The patient bite may include determined relationships between teeth in the upper dental arch and teeth in the lower dental arch.

For many prosthodontic procedures (e.g., to create a crown, bridge, veneer, etc.), an existing tooth of a patient is ground down to a stump. The ground tooth is referred to herein as a preparation tooth, or simply a preparation. The preparation tooth has a margin line (also referred to as a finish line), which is a border between a natural (unground) portion of the preparation tooth and the prepared (ground) portion of the preparation tooth. The preparation tooth is typically created so that a crown or other prosthesis can be mounted or seated on the preparation tooth. In many instances, the margin line of the preparation tooth is sub-gingival (below the gum line).

After a preparation tooth is created, a practitioner typically performs operations to ready that preparation tooth for scanning. Readying the preparation tooth for scanning may include wiping blood, saliva, etc. off of the preparation tooth and/or separating a patient's gum from the preparation tooth to expose the finish line. In some instances, a practitioner will insert a cord (also referred to as a dental wire) around the preparation tooth between the preparation tooth and the patient's gum. The practitioner will then remove the cord before generating a set of intraoral scans of the preparation tooth. The soft tissue of the gum will then revert back to its natural position, and in many cases collapses back over the finish line, after a brief time period. Accordingly, some of intraoral scan data 135A-N may include intraoral scans that were taken before the gum has collapsed over the margin line, and other intraoral scan data 135A-N may include intraoral scans that were taken after the gum has collapsed over the margin line. As a result, some intraoral scan data is superior to other intraoral scan data in depicting the preparation tooth, and in particular in depicting the margin line.

Intraoral scanners may work by moving the scanner 150 inside a patient's mouth to capture all viewpoints of one or more tooth. During scanning, the scanner 150 is calculating distances to solid surfaces in some embodiments. These distances may be recorded as images called 'height maps'. Each scan (e.g., optionally height map) is overlapped algorithmically, or 'stitched', with the previous set of scans to generate a growing 3D surface. As such, each scan is associated with a rotation in space, or a projection, to how it fits into the 3D surface.

During intraoral scanning, intraoral scan application 115 may register and stitch together two or more intraoral scans generated thus far from the intraoral scan session. In one embodiment, performing registration includes capturing 3D data of various points of a surface in multiple scans, and registering the scans by computing transformations between the scans. One or more 3D surfaces may be generated based on the registered and stitched together intraoral scans during the intraoral scanning. The one or more 3D surfaces may be output to a display so that a doctor or technician can view their scan progress thus far. As each new intraoral scan is captured and registered to previous intraoral scans and/or a 3D surface, the one or more 3D surfaces may be updated, and the updated 3D surface(s) may be output to the display. In embodiments, separate 3D surfaces are generated for the upper jaw and the lower jaw. This process may be performed in real time or near-real time to provide an updated view of the captured 3D surfaces during the intraoral scanning process.

When a scan session or a portion of a scan session associated with a particular scanning role (e.g., upper jaw role, lower jaw role, bite role, etc.) is complete (e.g., all scans for an intraoral site or dental site have been captured), intraoral scan application 115 may automatically generate a virtual 3D model of one or more scanned dental sites (e.g., of an upper jaw and a lower jaw). The final 3D model may be a set of 3D points and their connections with each other (i.e. a mesh). To generate the virtual 3D model, intraoral scan application 115 may register and stitch together the intraoral scans generated from the intraoral scan session that are associated with a particular scanning role. The registration performed at this stage may be more accurate than the registration performed during the capturing of the intraoral scans, and may take more time to complete than the registration performed during the capturing of the intraoral scans. In one embodiment, performing scan registration includes capturing 3D data of various points of a surface in multiple scans, and registering the scans by computing transformations between the scans. The 3D data may be projected into a 3D space of a 3D model to form a portion of the 3D model. The intraoral scans may be integrated into a common reference frame by applying appropriate transformations to points of each registered scan and projecting each scan into the 3D space.

In one embodiment, registration is performed for adjacent or overlapping intraoral scans (e.g., each successive frame of an intraoral video). In one embodiment, registration is performed using blended scans. Registration algorithms are carried out to register two adjacent or overlapping intraoral scans (e.g., two adjacent blended intraoral scans) and/or to register an intraoral scan with a 3D model, which essentially involves determination of the transformations which align one scan with the other scan and/or with the 3D model. Registration may involve identifying multiple points in each scan (e.g., point clouds) of a scan pair (or of a scan and the 3D model), surface fitting to the points, and using local searches around points to match points of the two scans (or of the scan and the 3D model). For example, intraoral scan application 115 may match points of one scan with the closest points interpolated on the surface of another scan, and iteratively minimize the distance between matched points. Other registration techniques may also be used.

Intraoral scan application 115 may repeat registration for all intraoral scans of a sequence of intraoral scans to obtain transformations for each intraoral scan, to register each intraoral scan with previous intraoral scan(s) and/or with a common reference frame (e.g., with the 3D model). Intraoral scan application 115 may integrate intraoral scans into a single virtual 3D model by applying the appropriate determined transformations to each of the intraoral scans. Each transformation may include rotations about one to three axes and translations within one to three planes.

In many instances, data from one or more intraoral scans does not perfectly correspond to data from one or more other intraoral scans. Accordingly, in embodiments intraoral scan application 115 may process intraoral scans (e.g., which may be blended intraoral scans) to determine which intraoral scans (or which portions of intraoral scans) to use for portions of a 3D model (e.g., for portions representing a particular dental site). Intraoral scan application 115 may use data such as geometric data represented in scans and/or time stamps associated with the intraoral scans to select optimal intraoral scans to use for depicting a dental site or a portion of a dental site (e.g., for depicting a margin line of a preparation tooth). In one embodiment, images are input into a machine learning model that has been trained to select and/or grade scans of dental sites. In one embodiment, one or more scores are assigned to each scan, where each score may be associated with a particular dental site and indicate a quality of a representation of that dental site in the intraoral scans.

Additionally, or alternatively, intraoral scans may be assigned weights based on scores assigned to those scans. Assigned weights may be associated with different dental sites. In one embodiment, a weight may be assigned to each scan (e.g., to each blended scan) for a dental site (or for multiple dental sites). During model generation, conflicting data from multiple intraoral scans may be combined using a weighted average to depict a dental site. The weights that are applied may be those weights that were assigned based on quality scores for the dental site. For example, processing logic may determine that data for a particular overlapping region from a first set of intraoral scans is superior in quality to data for the particular overlapping region of a second set of intraoral scans. The first intraoral scan data set may then be weighted more heavily than the second intraoral scan data set when averaging the differences between the intraoral scan data sets. For example, the first intraoral scans assigned the higher rating may be assigned a weight of 70% and the second intraoral scans may be assigned a weight of 30%. Thus, when the data is averaged, the merged result will look more like the depiction from the first intraoral scan data set and less like the depiction from the second intraoral scan data set.

Intraoral scan application 115 may generate one or more 3D models from intraoral scans, and may display the 3D models to a user (e.g., a doctor) via a user interface. The 3D models can then be checked visually by the doctor. The doctor can virtually manipulate the 3D models via the user interface with respect to up to six degrees of freedom (i.e., translated and/or rotated with respect to one or more of three mutually orthogonal axes) using suitable user controls (hardware and/or virtual) to enable viewing of the 3D model from any desired direction. The doctor may review (e.g., visually inspect) the generated 3D model of an intraoral site and determine whether the 3D model is acceptable (e.g., whether a margin line of a preparation tooth is accurately represented in the 3D model). In some embodiments, the intraoral scan application 115 automatically generates a sequence of views of the 3D model and scrolls through the views in the generated sequence. This may include zooming in, zooming out, panning, rotating, and so on.

Intraoral scan application 115 may include logic for automatically performing one or more operations traditionally performed manually by a user, referred to herein as smart scanning. A user may enter a smart scanning mode by making a selection to perform a smart scan from a user interface of intraoral scan application 115. Alternatively, intraoral scan application 115 may default to the smart scanning mode. At any time a user may select to exit the smart scanning mode. Multiple stages and work flows of intraoral scanning are provided, along with descriptions for each stage/work flow on how a user need to add input (apart from scanning) is removed.

In some embodiments, a volumetric model may include a virtual representation of an object in three dimensions in which internal regions (structures, etc.) are arranged within the volume in three physical dimensions in proportion and relative relation to the other internal and surface features of the object which is being modeled. For example, a volumetric representation of a tooth may include the outer surface as well as internal structures within the tooth (beneath the tooth surface) proportionately arranged relative to the tooth, so that a section through the volumetric model would substantially correspond to a section through the tooth, showing position and size of internal structures. In some embodiments, a volumetric model may be sectioned from any (e.g., arbitrary) direction and correspond to equivalent sections through the object being modeled. In some embodiments, a volumetric model may be an electronic or physical model. A physical volumetric model may be formed, e.g., by 3D printing, or the like. In some embodiments the volumetric models described herein may extend into the volume completely (e.g., through the entire volume, e.g., the volume of the teeth) or partially (e.g., into the volume being modeled for some minimum depth, e.g., 2 mm, 3 mm, 4 mm, 5 mm, 6 mm, 7 mm, 8 mm, 9 mm, 10 mm, 12 mm, etc.). In some embodiments, generating a model of a subject's teeth can include generating a 3D model or rendering of the teeth that include one or more of surface and internal features.

In some embodiments, any appropriate technique may be used to form the 3D models of the tooth including techniques that combine two or more or color images, 3D surface images and penetrative images. These 3D models may be referred to as combined 3D surface/volume models, 3D volumetric surface models, or simply "3D models," or the like herein. In some embodiments, both the surface data and the penetration imaging data may generally be in the same coordinate system. The two may be combined by using the common coordinate system. In some embodiments, the surface data may be expressed as a surface model and the internal features added to this model. In some embodiments, the data (both surface and internal features) may be reconstructed into a three-dimensional model concurrently (after adding together). In some embodiments, one or both datasets may be separately modified (e.g., filtered, subtracted, etc.). For example, forming the 3D model of the tooth including internal structures may comprise combing the 3D surface model data with an internal structure data (including volumetric data). Forming the 3D model of the tooth including internal structures may include combining one or more penetration images, where the penetration images may be taken from different illumination angles using the intraoral scanner.

In some embodiments, the 3D surface model data and/or internal structure data may be analyzed automatically or manually. In some embodiments, identifying features of interest, including crack and caries can be based on feature-recognition criterion (e.g., dark or light regions in the penetration images), pattern-recognition, machine learning, or the like. Features may be marked, including coloring, labeling or the like. Features may be marked directly in the 3D model, on the penetration image, or in a data structure that references (e.g., shares a coordinate system with) the 3D model of the tooth. For example, a machine learning model can be trained with input data including images and/or 3D models with or without caries or cracks and corresponding output data identifying whether a crack(s) and/or caries are located in the images and/or 3D models. The trained machine learning model can receive as input the scan data (e.g., images) and or 3D model created from a particular scan and output particular features of the images and/or 3D models that may be cracks and/or caries and a level of confidence (e.g., probability) that the identified features is a crack and/or caries.

Figure 2A:
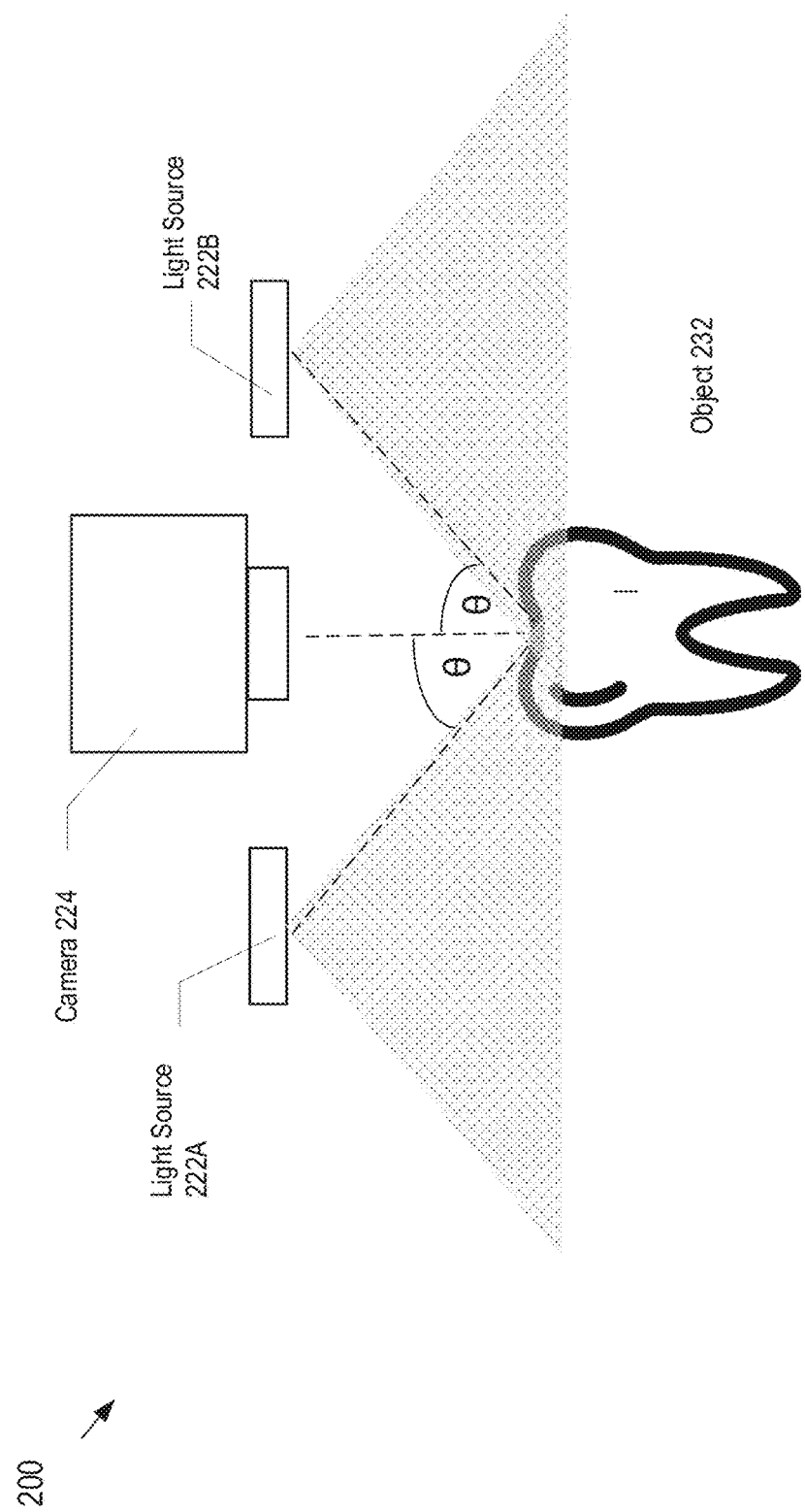
FIG. 2A illustrated elements of a wand configured to perform alternating illumination, in accordance with embodiments of the disclosure.

FIG. 2A illustrated elements of a wand configured to perform alternating illumination, in accordance with embodiments of the disclosure. Diagram 220 illustrates a part of wand with two light sources 222A and 222B (generally referred to as "light sources 222" herein), camera 224, and object 232. Light sources 222 can be similar to other light sources as described herein, such as light sources 22 of FIG. 1A. Camera 224 can similar to other light sources described herein, such as cameras 24 of FIG. 1A. Object 232 can similar to other objects described herein, such as object 32 or FIG. 1A. The dashed line extending from the camera 224 can reference the camera's optical axis, unless otherwise described.

In some embodiments, alternate illumination can be performed to capture scan data of an object 232. For example, alternate illumination can include an illumination technique where an object is illuminated from an initial angle with respect to the object (e.g., Illumination angle represented by angle θ between light source 222A and camera 224) at a first instance in time by a first light source (e.g., light source 222A), and illuminated from another angle with respect to the object (e.g., illumination angle represented by angle θ between light source 222B and optical axis of the camera 224) at a second instance in time by another light source (e.g., light source 222B). In some embodiments, the first instance in time and the second instance in time are sequential instances in time. I can be noted that although two illuminations by two different light sources are provided for purposes of illustration rather than limitation, in other embodiments any number of illuminations by any number of light sources (e.g., greater than two light sources) can be used in an alternate illumination operation. In some embodiments, the two or more different light sources are the same type of light sources (e.g., two different penetrative light sources). In some embodiments, alternate illumination can capture a sequence of scan data (e.g., sequence of images) of an object 232 where at each illumination instance the object is illuminated by a different light source positioned at a different physical location in the wand (e.g., not co-located so as to provide different illumination angles) and the reflected light from each illumination instance is captured by the same camera. In some embodiments, the illumination angle is less than 45 degrees. The illumination angle (θ) can refer to the angle between the direction of the light and the incident surface of the object normal (which also happens to be the optical axis of the camera 224 in FIG. 2A in this instance, but can be different than the optical axis of the camera if the camera is aligned differently with respect to the object).

Some illumination techniques, such as trans-illumination use strong illumination that can saturate image areas, which results in the loss of image information (e.g., loosing contrast data). In alternate illumination, the light sources 222 and camera 224 are arranged in such a manner, as illustrated in FIG. 2A that scan data is captured for different illumination angles. The scan data taken as a whole from alternate illumination includes fewer saturated image areas and hence, greater image information than other techniques.

Figure 2B:
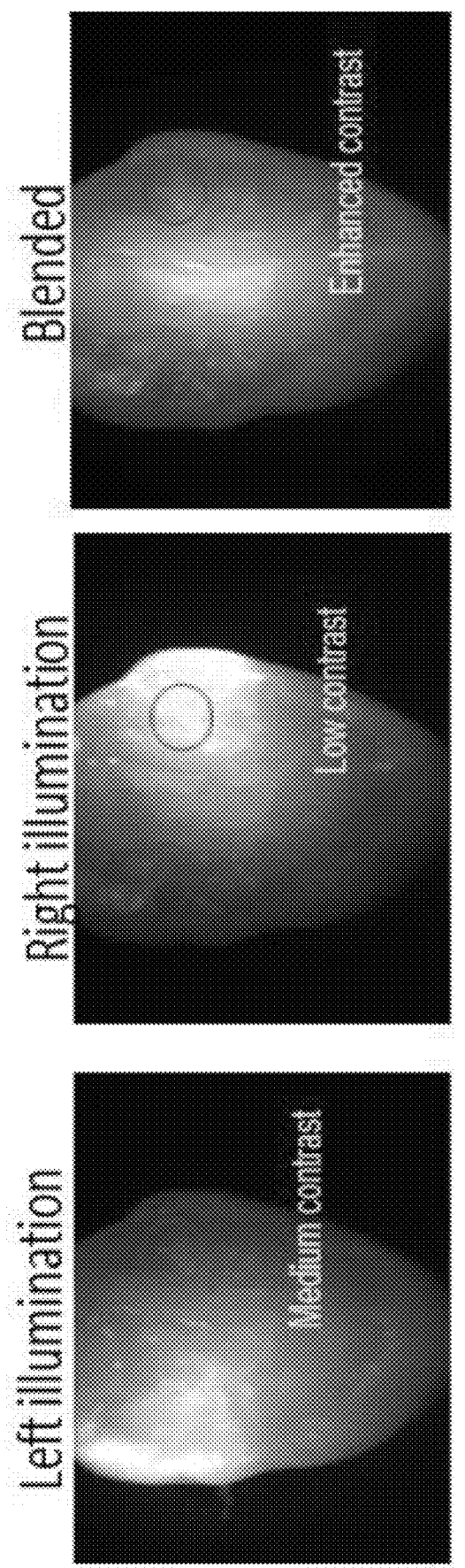
FIG. 2B illustrates scan data from a scan using alternate illumination, in accordance with embodiments of the disclosure.

FIG. 2B illustrates scan data from a scan using alternate illumination, in accordance with embodiments of the disclosure. In some embodiments, an image 252A of the object 232 can be taken using illumination from light source 222A (left illumination) at an instance in time and another image 252B of the object 232 can be taking using light source 222B (right illumination) at another instance of time. The image 252A using left illumination can have some saturated image areas to the left side of the object and some medium contrast areas to the right of the object (e.g., circled). The image 252B using right illumination can have some saturated image areas to the right side of the object (e.g., circled) and some medium contrast areas to the left side of the object. A blended image 252C can be created using image 252A and 252B (e.g., image based on left illumination and image based on right illumination) that reduces the saturated image areas (as compared to any single image 252A or 252B). In some embodiments, the scan data of alternate illumination (e.g., image based on left illumination and image based on right illumination) can be combined (also referred to as "blended" herein) to generate blended scan data (e.g., blended image) of the object with improved contrast. Blended images are further described with respect to FIG. 4.

In some embodiments, the scan data (e.g., images) acquired from alternate illumination may be combined (e.g., blended) and used to generated a 3D model. In other embodiments, the scan data acquired from alternate illumination may not be combined and used to generate a 3D model.

In some embodiments, alternate illumination can be used with any type of light source, including but not limited to penetrative light projectors, structured light projectors, uniform light projectors, or a combination thereof. Example sequences of alternate illumination are provide in FIG. 3A-3G.

In some embodiments, alternate illumination can be used along (e.g., combined) with polarization techniques as described herein. In some embodiments, alternate illumination can be used separate from the polarization techniques, as described herein.

FIGS. 3A-3G illustrate various illumination sequences, in accordance with embodiments of the disclosure. Each of FIGS. 3A-3G illustrate a graph having a vertical axis indicating an illumination source (e.g., light source) and a horizontal axis representing time. The illumination sources include uniform light projectors, structured light projectors, and penetrative light projectors. The small rectangular box in the cells of the graph represent the duration of the illumination source pulse. At each cell where an illumination source pulse is illustrated, scan data can be captured that corresponds to the respective illumination pulse. The scan data can include image data, such as an image of the dental site.

Figure 3A:
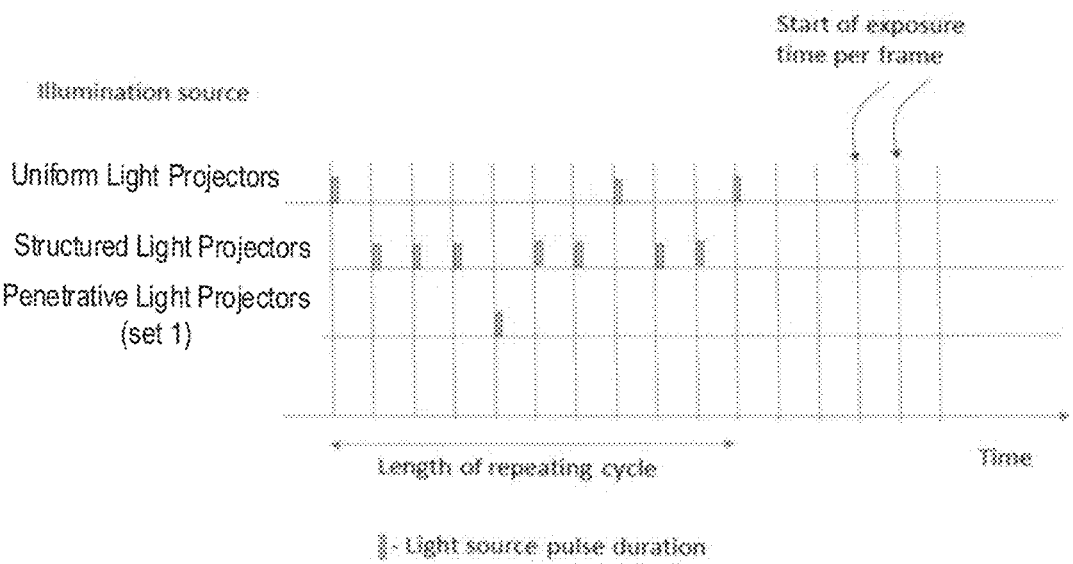
FIGS. 3A-3G illustrate various illumination sequences, in accordance with embodiments of the disclosure.

FIG. 3A illustrates an illumination sequence, in accordance with embodiments of the disclosure. For example, in FIG. 3A ten pulses are represented and the 10 pulses correspond to 2 uniform light images (e.g., color images), 1 penetrative light image (e.g., 1 NIR image) and 7 structured light images. The set of pulses can correspond to an illumination sequence. The illumination sequence represented in FIG. 3A includes uniform light pulse, structured light pulse, structured light pulse, structured light pulse, penetrative light pulse, structured light pulse, structured light pulse, uniform light pulse, structured light pulse, structured light pulse, and uniform light pulse. The sequence of light pulses in an illumination sequence are illustrated in FIG. 3B-3G in a similar manner as illustrated in FIG. 3A, and are not further recited below for the sake of brevity.

In some embodiments, the particular illumination sequence can be repeated. In some embodiments, different illumination sequences can be combined sequentially. For example, the illumination sequence illustrated in FIG. 3A can be sequentially followed by the illumination sequence illustrated in FIG. 3B and the two illumination sequences can be repeated as desired. In some embodiments, elements of one illumination sequence can be mixed with other elements of another illumination sequence. In some embodiments, elements of an illumination sequence can be used without other elements of the illumination sequence. The illumination sequences illustrated in FIGS. 3A-3G are provided for purposes of illustration, rather than limitation.

Figure 3B:
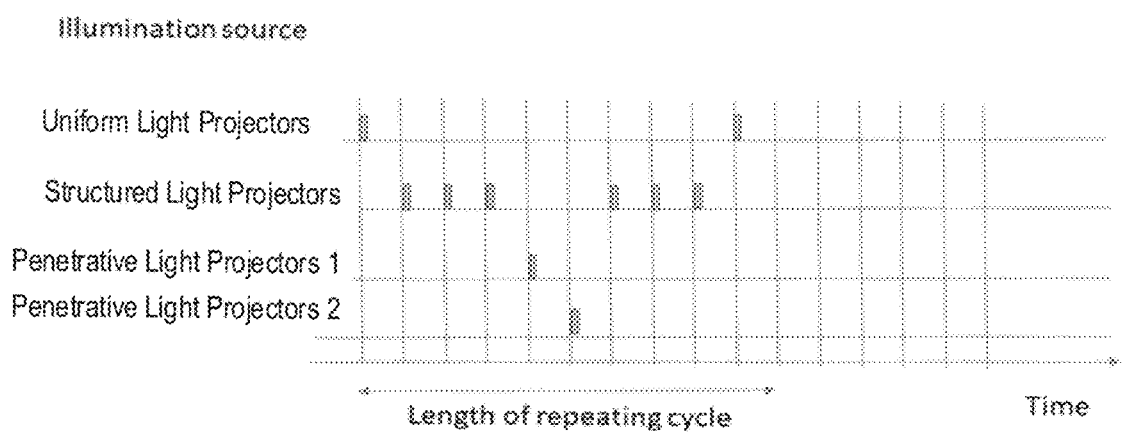

FIG. 3B illustrates an illumination sequence that includes alternate illumination using penetrative light projectors, in accordance with embodiments described herein. As illustrated, penetrative light projectors 1 (e.g., one or more light projectors) produce a penetrative light pulse(s) (e.g., left light source 222A or FIG. 2A) at an instance of time and penetrative light projectors 2 1 (e.g., one or more different light projectors) produce a penetrative light pulse(s) (e.g., right light source 222B of FIG. 2B) and another instance in time. The two instances in time are sequential. It can be noted that alternate illumination is shown using penetrative light projectors for purpose of illustration, rather than limitation. In other embodiments, other types of light sources can be configured for alternate illumination.

Figure 3C:
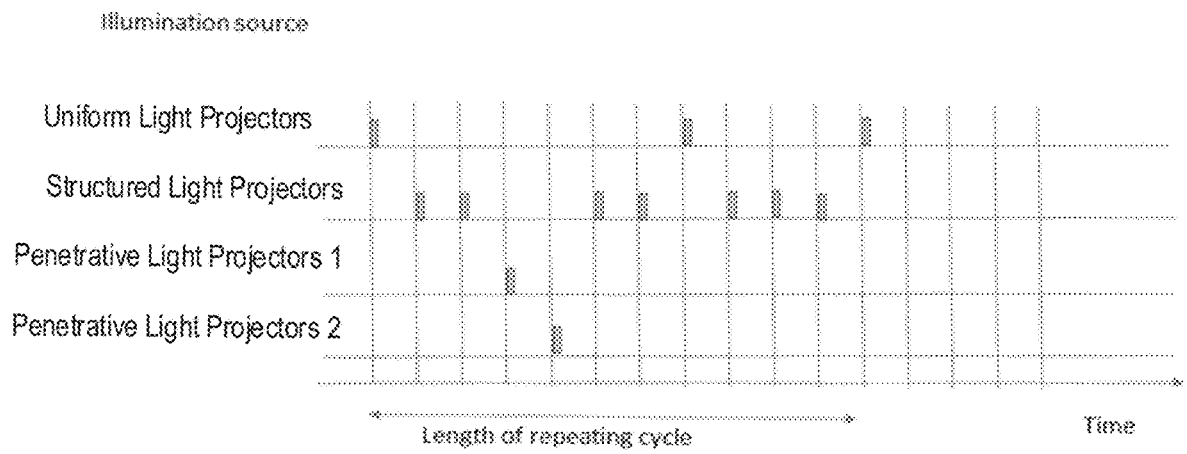

FIG. 3C illustrates another illumination sequence that includes alternate illumination using penetrative light projectors, in accordance with embodiments of the disclosure. FIG. 3B and FIG. 3C are similar but for the number of structured light pulses and uniform light pulses in FIG. 3C is greater. In some embodiments, in an alternate illumination sequence two different penetrative light pulses can be separated by a different type of light pulse, such as a structured light pulse.

Figure 3D:
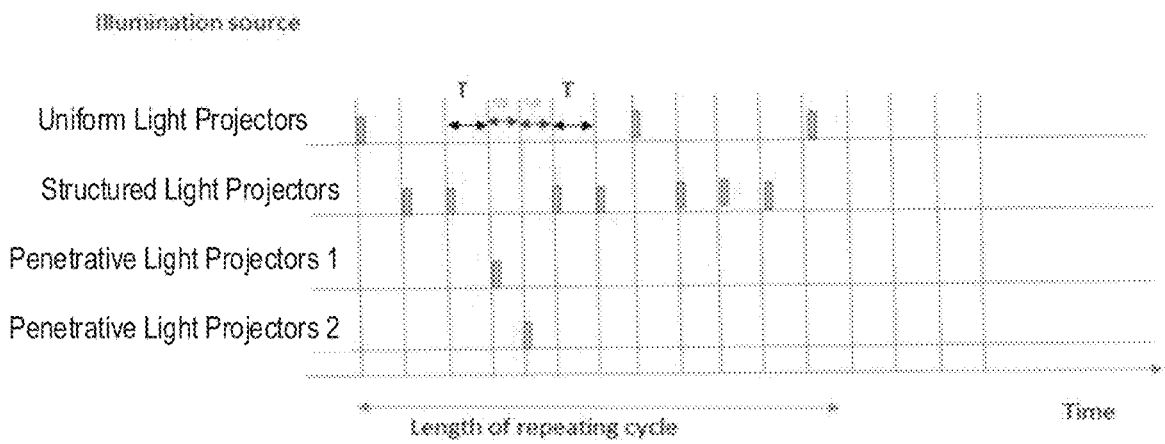

FIG. 3D illustrates another illumination sequence that includes alternate illumination using penetrative light projectors, in accordance with embodiments of the disclosure. The alternate illumination (e.g., the sequential penetrative light pulses) can be performed at a higher frame rate, which may result in higher temporal resolution and lower spatial resolution. As illustrated, the higher frame rate of the penetrative light pulses is relative to the pulses of the other types of light sources. In the example, the time period between penetrative light pulses is half the time period between light pulses of the other types of light sources.

Figure 3E:
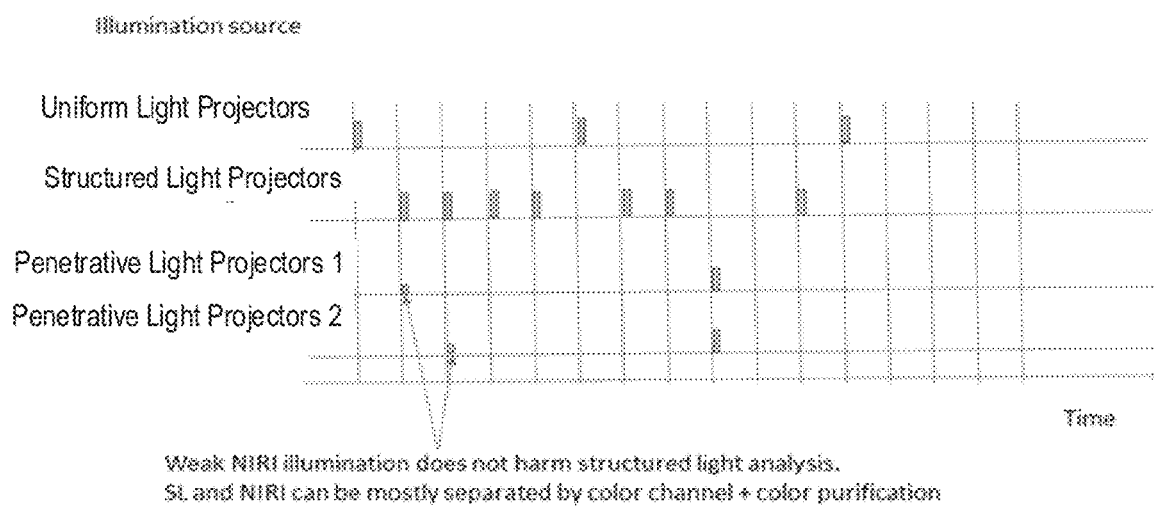
Figure 3F:
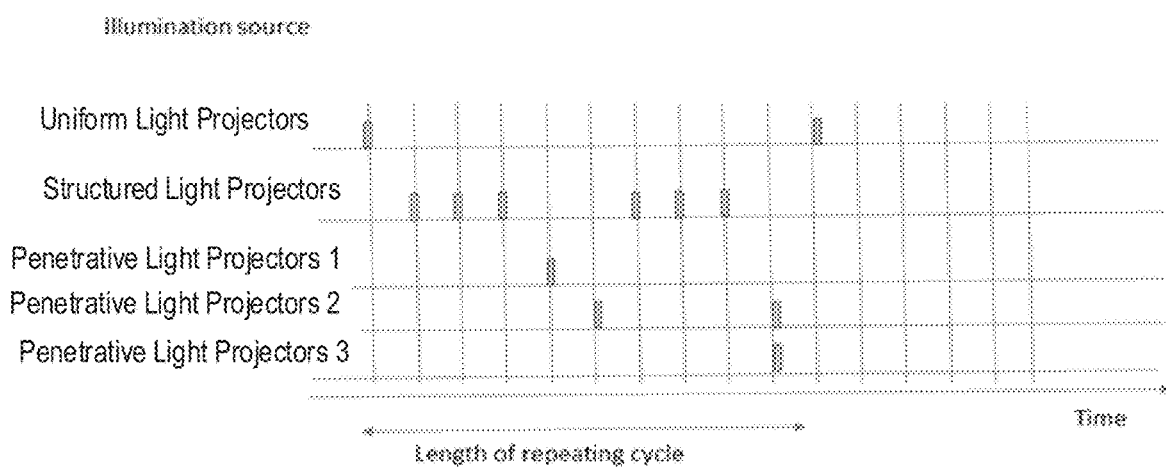
Figure 3G:
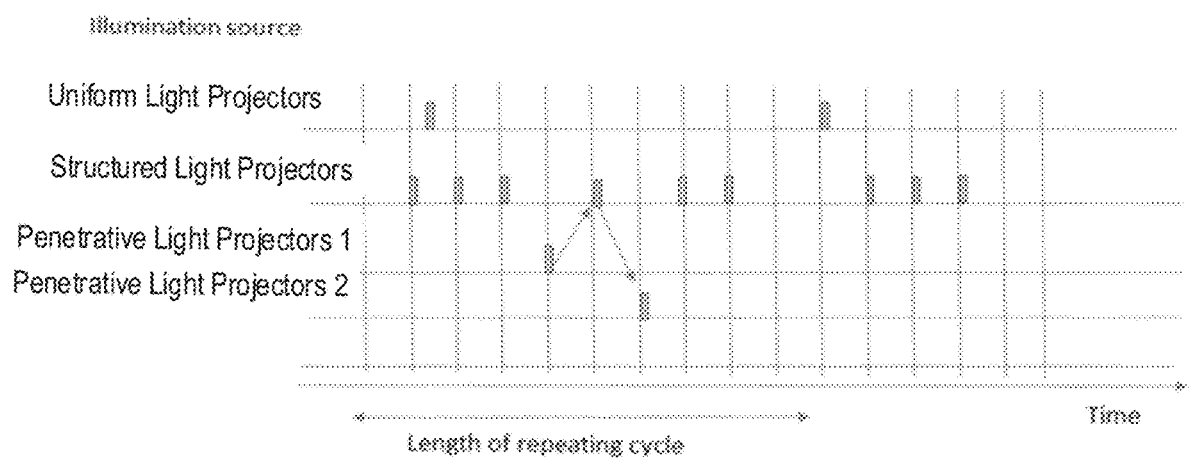

FIG. 3E illustrates another illumination sequence that includes alternate illumination using penetrative light projectors. In some embodiments, alternate illumination of a particular type of light pulse, such as penetrative light pulses shown in the $2^{nd}$ and $3^{rd}$ position of the illumination sequence, can be performed concurrently with another type of illumination, such as structured light pulses as also shown in the $2^{nd}$ and $3^{rd}$ position of the illumination sequence. In the above example, for each time period a structured light image and a penetrative light image can be obtained. In some embodiments, different frequencies of light between the two types of light pulses can help reduce interference. For example, the structured light pulses can be green and blue light, which can be sensed by blue and green Bayer filter pixels of the camera while the penetrative light sources can be sensed by all pixels (e.g., red, green and blue (RGB)). In another example, some of the pixels of the camera sensor can be configured with a particular filter (e.g., NIR filter) such that only or mostly penetrative light information is captured with the filtered pixel. In still another example, information from the penetrative light pulse can be separate from information from the structured light pulse (e.g., green and blue light) using one or more of a color filter, such as a Bayer filter, and a color purification algorithm. For instance, the color purification algorithm for the penetrative light pulses can include computing a grey level (which equals red−a1xblue−a2xgreen). For every pixel red that is stronger than blue or green the computed grey level is used. For every pixel where the blue and/or red signal are stronger than red, the red signal from neighboring pixels is used.

In another embodiment, two sets of the same type of light sources can be illuminated concurrently. For instance, at position 9 of the illumination sequence the penetrative light pulses are emitted concurrently. This may result in a single image, in some cases.

FIG. 3E illustrates another illumination sequence that includes alternate illumination using penetrative light projectors, in accordance with embodiments of the disclosure. As illustrated, more than two sets of a particular type of light source can be used. For example, three sets of penetrative light sources can be operated independently from one another. The multiple sets of the same type of light source can be used in different combinations. For example, penetrative light projector 1 and penetrative light projector 2 are configured to perform alternate illumination at position 5 and position 6 of the illumination sequence. Penetrative light projector 2 and penetrative light projector 3 are configured to perform concurrent illumination at position 10 of the sequence.

FIG. 3E illustrates another illumination sequence that includes alternate illumination using penetrative light projectors, in accordance with embodiments of the disclosure. In some embodiments, in an alternate illumination technique two light pulses of the same type used for the alternate illumination can have one or more other light pulses of a different type sequence between them. For example, the structured light pulse at position 5 is between the penetrative light pulses at position 4 and position 6.

In some embodiments, the illumination sequence can be predetermined and defined prior to run time of the scan. In still other embodiments, an illumination sequence does not need to be defined in advance. The illumination sequence can be determined dynamically at run-time (during the scan). For instance, an illumination sequence algorithm can estimate the available contrast in real time, determined the information needed, and arrange the illumination sequence accordingly.

The methods described herein, such as method 400, 500 and 600 and/or each of any method's individual functions, routines, subroutines, or operations can be performed by a processing device, having one or more processing units (CPU) and memory devices communicatively coupled to the CPU(s). In some implementations, methods 400, 500 or 600 can be performed by a single processing thread or alternatively by two or more processing threads, each thread executing one or more individual functions, routines, subroutines, or operations of the method. The methods 400, 500 or 600 as described below can be performed by processing logic that can include hardware (e.g., processing device, circuitry, dedicated logic, programmable logic, microcode, hardware of a device, integrated circuit, etc.), software (e.g., instructions run or executed on a processing device), or a combination thereof. In some embodiments, methods 400, 500 or 600 are performed by alternate illumination and controlled polarization module 120 described in FIG. 1D. Although shown in a particular sequence or order, unless otherwise specified, the order of the operations can be modified. Thus, the illustrated embodiments should be understood only as examples, and the illustrated operations can be performed in a different order, while some operations can be performed in parallel. Additionally, one or more operations can be omitted in some embodiments. Thus, not all illustrated operations are required in every embodiment, and other process flows are possible. In some embodiments, the same, different, fewer, or greater operations can be performed. Reference is made to elements of other Figures to help illustrate the methods 400, 500 or 600.

Figure 4:
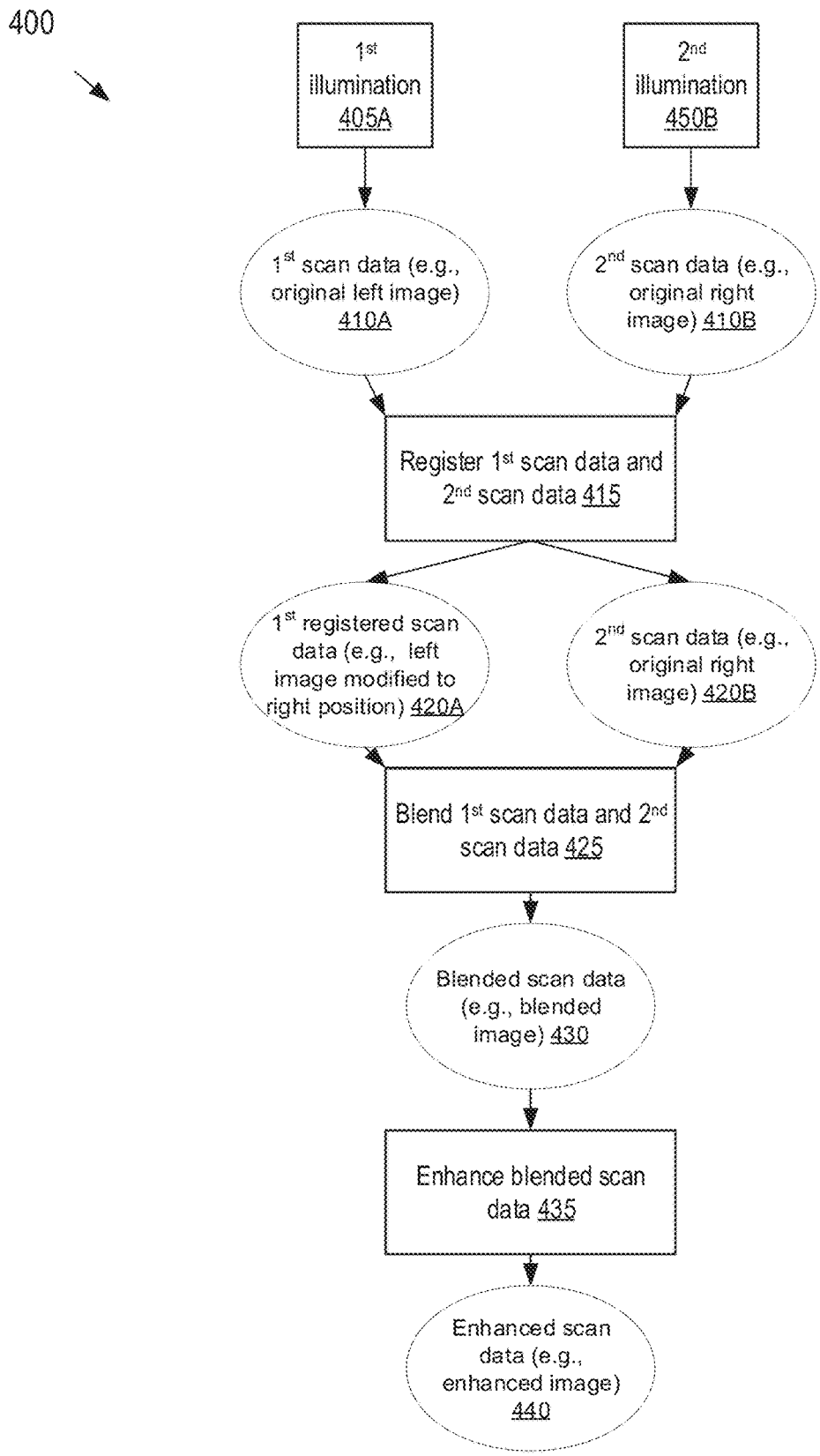
FIG. 4 depicts a flow diagram of an example method for combining images acquired using alternate illumination, in accordance with some embodiments of the disclosure.

FIG. 4 depicts a flow diagram of an example method 400 for combining images acquired using alternate illumination, in accordance with some embodiments of the disclosure. Operation 450A and operation 450B illustrate an alternate illumination sequence, as described herein. For example, at operation 405A the wand illuminates the dental site using a first light source of a first light source type and from a first illumination angle. At operation 405B, the wand illuminates the dental site using a second light source of the same light source type and from a second illumination angle. In some embodiments, the first illumination (e.g., operation 405A) can immediately precede the second illumination (e.g., operation 450B).

At operation 410A and operation 410B, respective scan data from the first and second illumination can be acquired. The first scan data (e.g., operation 410A) can include image data from a first illumination angle (e.g., original left image). The second scan data (e.g., operation 410B) can include image data from the second illumination angle (e.g. original right image).

At operation 415, the $1^{st}$ scan data (e.g., original left image) from operation 410A can be registered with the second scan data (e.g., original right image) to generate registration data. Registration of scan data is further described at least with respect to FIG. 1D.

In some embodiments, to perform registration a 3D model can be created using other scan data, such as scan data acquired from illumination using structured light projectors. In some embodiments, the $1^{st}$ scan data and the $2^{nd}$ scan data can be scan data acquired from illumination from penetrative light projectors, such as NIR light projectors. The registration data can be acquired by projecting the $1^{st}$ scan data and the $2^{nd}$ scan data onto the 3D model and arranging the $1^{st}$ scan data and the $2^{nd}$ scan data in corresponding positions in the coordinate system of the 3D model. In some embodiments, the scan data acquired from illumination using structured light projectors can be captured in the same illumination sequence as the $1^{st}$ scan data and the $2^{nd}$ scan data acquired from illumination from penetrative light projectors. When projected on a 3D model, the $1^{st}$ scan data and the $2^{nd}$ scan data can be arranged so that each pixel of the $1^{st}$ scan data and the $2^{nd}$ scan data converge.

In some embodiments, optical flow registration can be performed to register the $1^{st}$ scan data and the $2^{nd}$ scan data.

For example, the displacement (e.g., local displacement field) between each pixel (or voxel) of the $1^{st}$ scan data and each respective pixel (or voxel) of the $2^{nd}$ scan data can be determined. An optimal displacement value (e.g., minimum displacement value) can be determined and applied to other pixels of the $1^{st}$ scan data (or $2^{nd}$ scan data). In some embodiments, the optical displacement value can also identify or account for the contrast for each pixel (or voxel) of the $1^{st}$ scan data and the $2^{nd}$ scan data. The pixel with the highest contrast (but lower than a threshold) can be selected.

At operation 420A, the $1^{st}$ registered scan data (e.g., left image modified to right position) is acquired. At operation 420B, the $2^{nd}$ scan data (e.g., original right image) is acquired.

At operation 425, a blending operation can be performed to blend the $1^{st}$ registered scan data with the $2^{nd}$ scan data to generate blended scan data. The blended scan data can incorporate features of the $1^{st}$ registered scan data and features of $2^{nd}$ scan data into new scan da (e.g., blended scan data including a single unified image). In some embodiments, Poisson blending techniques can be incorporated in operation 425. For example, an image can be reconstructed from gradients and a number of boundary conditions. In some embodiments, rather than boundary conditions a localization factor can be implemented. In some embodiments, the gradients can be calculated using finite element analysis (rather than difference in gradient between the $1^{st}$ and $2^{nd}$ scan data).

At operation 430, blended scan data is acquired. The blended scan data can include a blended image of the dental site.

At operation 435, an enhancement operation can be performed on the blended scan data to generated enhanced scan data. The enhancement operation can apply one or more filters to the blended scan data to enhance the associated blended image. For example, the enhancement operation can include the application of bilateral filters or contrast enhancement filters, among other.

At operation 440, enhanced scan data (e.g., enhanced image) of the dental site is acquired.

Figure 5:
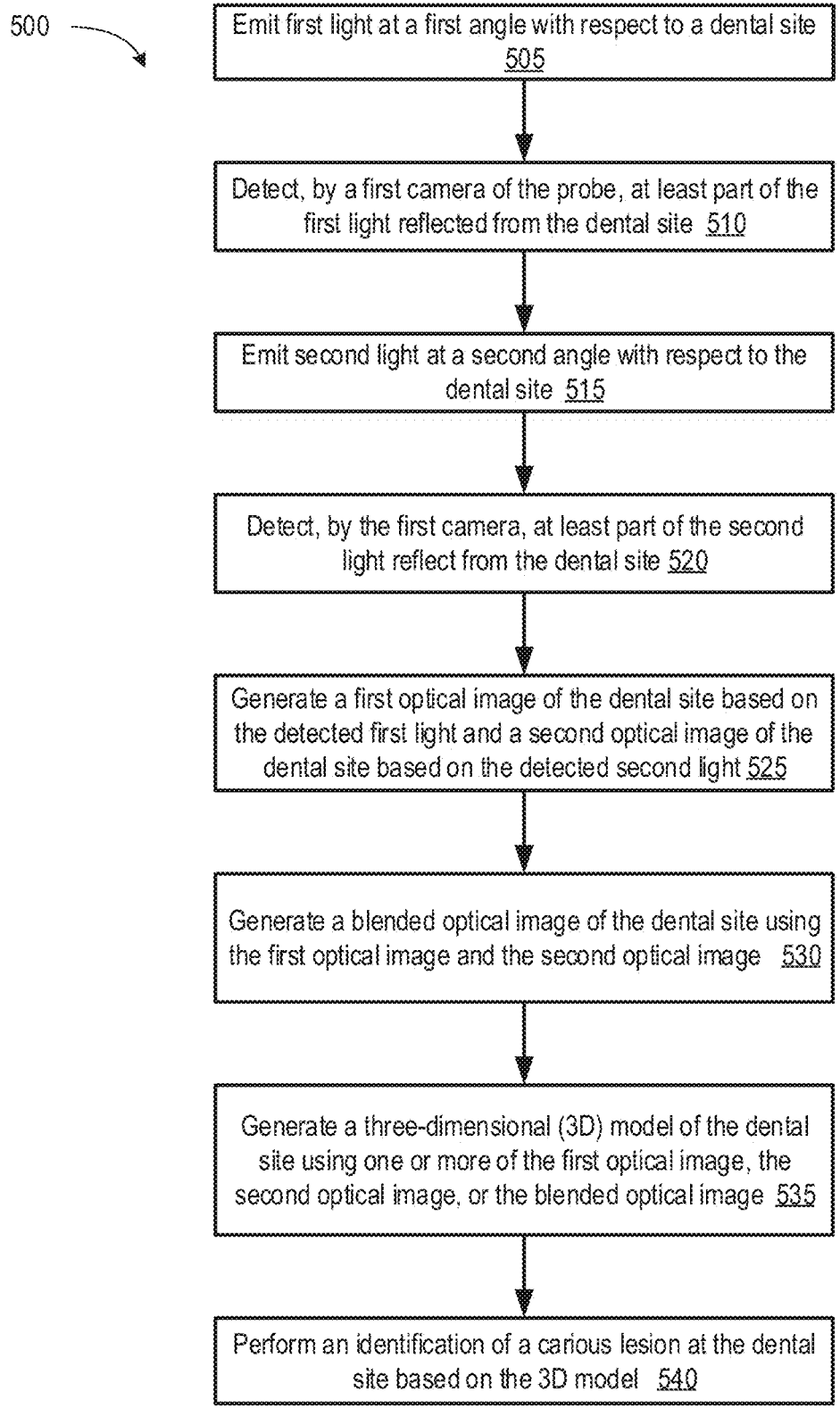
FIG. 5 depicts a flow diagram of an example method of using alternate illumination to generate images of a dental site, in accordance with some embodiments of the disclosure.

FIG. 5 depicts a flow diagram of an example method 500 of using alternate illumination to generate images of a dental site, in accordance with some embodiments of the disclosure.

At operation 505, processing logic emits first light at a first angle with respect to a dental site (e.g., first illumination angle). In some embodiments, processing logic emits the first light at a first instance in time by a first light source of a probe of an intraoral scanner.

At operation 510, processing logic detects, by a first camera of the probe, at least part of the first light reflected from the dental site.

In some embodiments, detecting, by the first camera of the probe, the at least part of the first light reflected from the dental site includes detecting the at least part of the first light reflected from the dental site that is filtered by a polarizing filter having a first polarization axis.

At operation 515, processing logic emits second light at a second angle with respect to the dental site (e.g., second illumination angle). In some embodiments, processing logic emits the second light at a second instance in time by a second light source of the probe.

In some embodiments, the first instance in time and the second instance in time are sequential instances in time.

In some embodiments, the first light source and the second light source are both from one of patterned light sources configured to emit a pattern of light, un-patterned light sources configured to emit un-patterned light, or NIR light sources configured to emit NIR light. In some embodiments, the first light source and the second source are different light sources of the same type of light source.

In some embodiments, the first light source and the second light source are from different ones of patterned light sources configured to emit a pattern of light, un-patterned light sources configured to emit un-patterned light, or a near infrared (NIR) light sources configured to emit NIR light.

At operation 520, processing logic detects, by the first camera, at least part of the second light reflect from the dental site.

In some embodiments, detecting, by the first camera, the at least part of the second light reflect from the dental site includes detecting the at least part of the second light reflected from the dental site that is filtered by the polarizing filter having a first polarization axis.

In some embodiments, each of the first light source and the second light source is a different one of multiple patterned light sources and each is configured to emit a pattern of light at a second polarization axis. The first polarization axis is substantially parallel to the second polarization axis.

In some embodiments, each of the first light source and the second light source is a different one multiple near infrared (NIR) light sources and is configured to emit NIR light at a third polarization axis. The first polarization axis is substantially perpendicular to the third polarization axis.

At operation 525, processing logic generates a first optical image of the dental site based on the detected first light and a second optical image of the dental site based on the detected second light.

At operation 530, processing logic generates a blended optical image of the dental site using the first optical image and the second optical image.

At operation 535, processing logic generates a three-dimensional (3D) model of the dental site using one or more of the first optical image, the second optical image, or the blended optical image. In some embodiments, the processing logic generates a three-dimensional (3D) model of the dental site using the first optical image and the second optical image. In some embodiments, the processing logic generates a three-dimensional (3D) model of the dental site using the blended optical image.

At operation 540, processing logic performs an identification of a carious lesion at the dental site based on the 3D model of the dental site. In some embodiments, the first optical image is a first near infrared (NIR) image, the second optical image is a second NIR image and the blended optical image is a blended NIR image.

Figure 6:
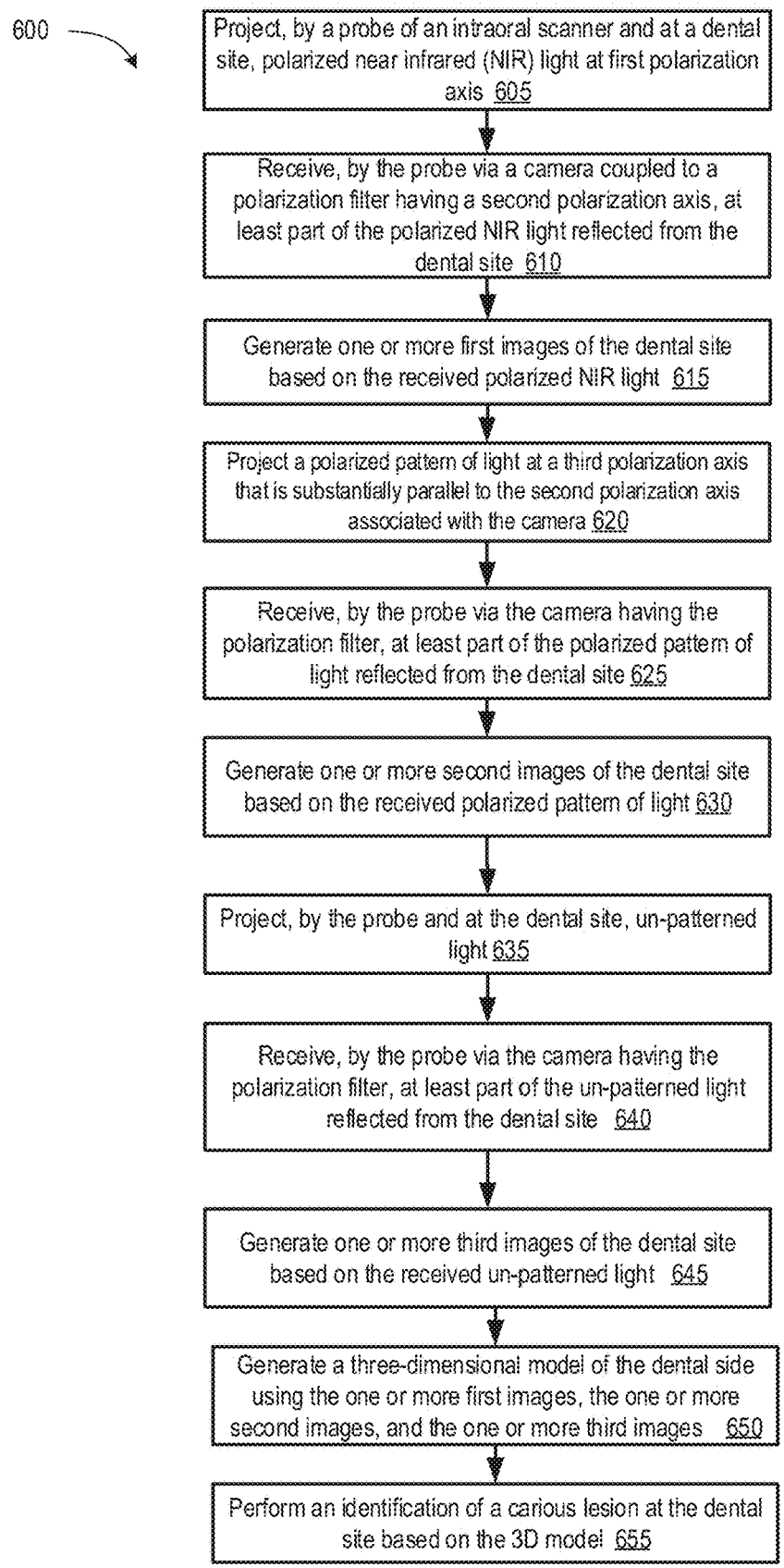
FIG. 6 depicts a flow diagram of an example method of using controlled polarization to generate images of a dental site, in accordance with some embodiments of the disclosure.

FIG. 6 depicts a flow diagram of an example method 600 of using controlled polarization to generate images of a dental site, in accordance with some embodiments of the disclosure.

At operation 605, processing logic projects, by a probe of an intraoral scanner and at a dental site, polarized near infrared (NIR) light at first polarization axis.

In some embodiments, projecting the polarized NIR light at the first polarization axis includes emitting, at a first instance in time by a first NIR light source of the probe, first polarized NIR light at a first angle with respect to the dental site, and emitting, at a second instance in time by a second NIR light source of the probe. The second polarized NIR light is emitted at a second angle with respect to the dental site.

In some embodiments, the first instance in time and the second instance in time are first sequential instances in time.

At operation 610, processing logic receives, by the probe via a camera coupled to a polarization filter having a second polarization axis, at least part of the polarized NIR light reflected from the dental site. In some embodiments, the first polarization axis is substantially perpendicular to the second polarization axis.

In some embodiments, receiving the at least part of the polarized NIR light reflected from the dental site includes detecting, by the camera having the polarization filter, at least part of the first polarized NIR light reflected from the dental site. Processing logic detects, by the camera having the polarization filter, at least part of the second polarized NIR light reflect from the dental site.

At operation 615, processing logic generates one or more first images of the dental site based on the received polarized NIR light.

In some embodiments, generating the one or more first images of the dental site based on the received polarized NIR light includes generating a first optical image of the dental site based on the detected first polarized NIR light and a second optical image of the dental site based on the detected second polarized NIR light.

In some embodiments, the first optical image includes a first NIR optical image and the second optical image includes a second NIR optical image. Processing logic can further generate a blended NIR optical image of the dental site using the first optical image and the second optical image.

At operation 620, processing logic projecting a polarized pattern of light at a third polarization axis that is substantially parallel to the second polarization axis associated with the camera. In some embodiments, the polarized pattern of light at a third polarization axis is projected by the probe and at the dental site.

In some embodiments, projecting the polarized pattern of light at the third polarization axis that is substantially parallel to the second polarization axis associated with the camera includes emitting, at a third instance in time by a first patterned light source of the probe, first polarized pattern of light at a third angle with respect to the dental site. Processing logic emits, at a fourth instance in time by a second patterned light source of the probe, second polarized pattern of light at a fourth angle with respect to the dental site.

In some embodiments, the third instance in time and the fourth instance in time are second sequential instances in time.

At operation 625, processing logic receives, by the probe via the camera having the polarization filter, at least part of the polarized pattern of light reflected from the dental site.

In some embodiments, receiving the at least part of the polarized pattern of light reflected from the dental site includes detecting, by the camera having the polarization filter, at least part of the first polarized pattern of light reflected from the dental site. Processing logic detects, by the camera having the polarization filter, at least part of the second polarized pattern of light reflect from the dental site.

At operation 630, processing logic generates one or more second images of the dental site based on the received polarized pattern of light.

In some embodiments, generating the one or more second images of the dental site based on the received polarized pattern of light includes generating a third optical image of the dental site based on the detected first polarized pattern of light and a fourth optical image of the dental site based on the detected second polarized pattern of light.

At operation 635, processing logic projects, by the probe and at the dental site, un-patterned light.

At operation 640, processing logic receives, by the probe via the camera having the polarization filter, at least part of the un-patterned light reflected from the dental site.

At operation 645, processing logic generates one or more third images of the dental site based on the received un-patterned light.

At operation 650, processing logic generates a three-dimensional model of the dental site using the one or more first images of the dental site generated based on the received polarized NIR light, the one or more second images of the dental site generated based on the received polarized pattern of light, and the one or more third images of the dental site generated based on the received un-patterned light.

At operation 655, processing logic performs an identification of a carious lesion at the dental site based on the 3D model.

Figure 7:
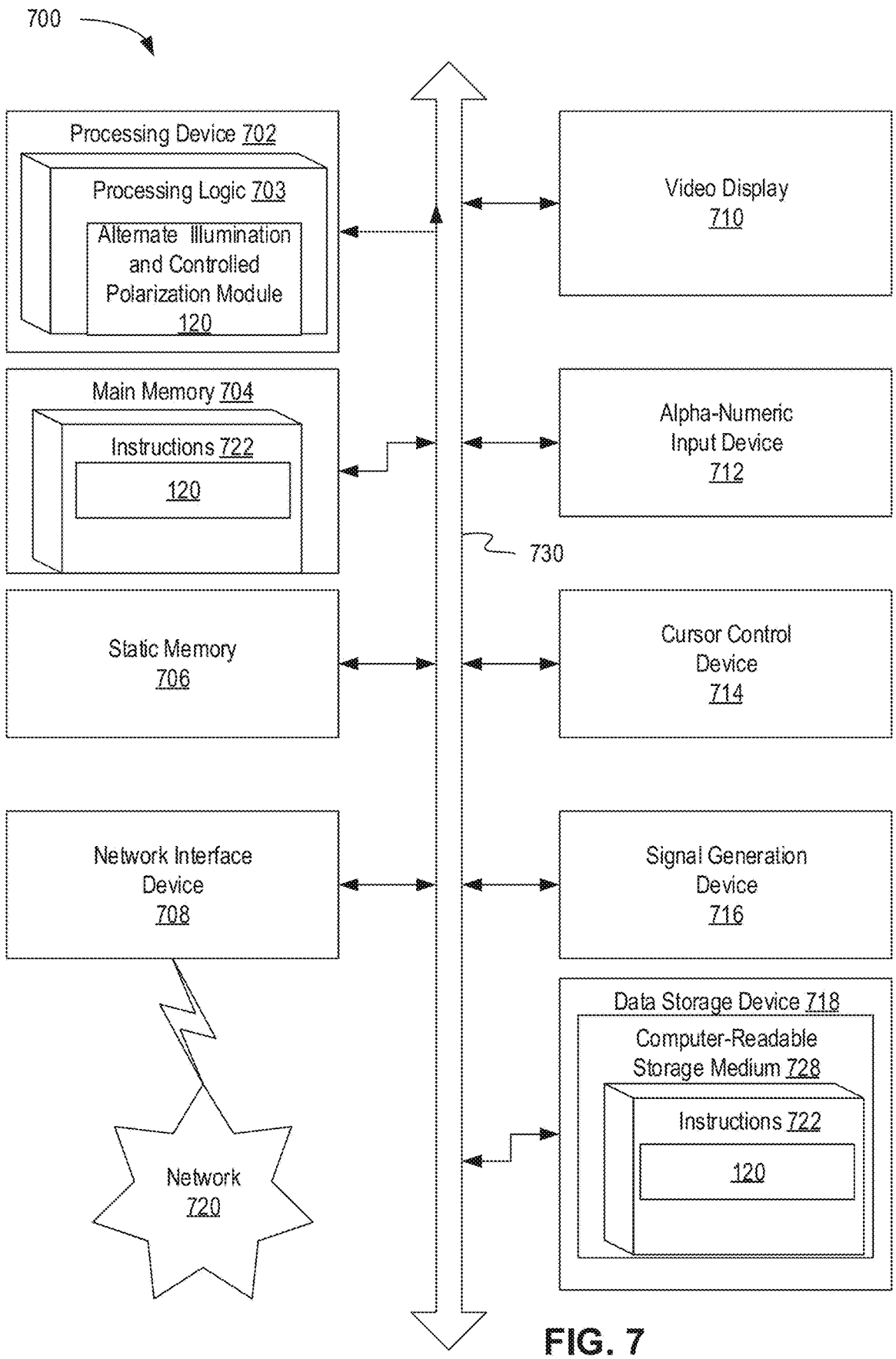
FIG. 7 depicts a block diagram of an example computer device within which a set of instructions, for causing the machine to perform any of the one or more methodologies discussed herein can be executed, in accordance with some implementations of the disclosure.

FIG. 7 depicts a block diagram of an example computer device 700 within which a set of instructions, for causing the machine to perform any of the one or more methodologies discussed herein can be executed, in accordance with some implementations of the disclosure. Example computer device 700 can be connected to other computer devices in a LAN, an intranet, an extranet, and/or the Internet. Computer device 700 can operate in the capacity of a server in a client-server network environment. Computer device 700 can be a personal computer (PC), a set-top box (STB), a server, a network router, switch or bridge, or any device capable of executing a set of instructions (sequential or otherwise) that specify actions to be taken by that device. Further, while only a single example computer device is illustrated, the term "computer" shall also be taken to include any collection of computers that individually or jointly execute a set (or multiple sets) of instructions to perform any one or more of the methods discussed herein.

Example computer device 700 can include a processing device 702 (also referred to as a processor or CPU), which can include processing logic 703, a main memory 704 (e.g., read-only memory (ROM), flash memory, dynamic random access memory (DRAM) such as synchronous DRAM (SDRAM), etc.), a static memory 706 (e.g., flash memory, static random access memory (SRAM), etc.), and a secondary memory (e.g., a data storage device 718), which can communicate with each other via a bus 730.

Processing device 702 represents one or more general-purpose processing devices such as a microprocessor, central processing unit, or the like. More particularly, processing device 702 can be a complex instruction set computing (CISC) microprocessor, reduced instruction set computing (RISC) microprocessor, very long instruction word (VLIW) microprocessor, processor implementing other instruction sets, or processors implementing a combination of instruction sets. Processing device 702 can also be one or more special-purpose processing devices such as an application specific integrated circuit (ASIC), a field programmable gate array (FPGA), a digital signal processor (DSP), network processor, or the like. In accordance with one or more aspects of the disclosure, processing device 702 can be configured to execute instructions performing any of the operations performed by alternate illumination and controlled polarization module 120.

Example computer device 700 can further comprise a network interface device 708, which can be communicatively coupled to a network 720. Example computer device 700 can further comprise a video display 710 (e.g., a liquid crystal display (LCD), a touch screen, or a cathode ray tube (CRT)), an alphanumeric input device 712 (e.g., a keyboard), a cursor control device 714 (e.g., a mouse), and an acoustic signal generation device 716 (e.g., a speaker).

Data storage device 718 can include a computer-readable storage medium (or, more specifically, a non-transitory computer-readable storage medium) 728 on which is stored one or more sets of executable instructions 722. In accordance with one or more aspects of the disclosure, executable instructions 722 can comprise executable instructions to perform any of the operations of alternate illumination and controlled polarization module 120.

Executable instructions 722 can also reside, completely or at least partially, within main memory 704 and/or within processing device 702 during execution thereof by example computer device 700, main memory 704 and processing device 702 also constituting computer-readable storage media. Executable instructions 722 can further be transmitted or received over a network via network interface device 708.

While the computer-readable storage medium 728 is shown in FIG. 7 as a single medium, the term "computer-readable storage medium" should be taken to include a single medium or multiple media (e.g., a centralized or distributed database, and/or associated caches and servers) that store the one or more sets of VM operating instructions. The term "computer-readable storage medium" shall also be taken to include any medium that is capable of storing or encoding a set of instructions for execution by the machine that cause the machine to perform any one or more of the methods described herein. The term "computer-readable storage medium" shall accordingly be taken to include, but not be limited to, solid-state memories, and optical and magnetic media.

Some portions of the preceding detailed descriptions have been presented in terms of algorithms and symbolic representations of operations on data bits within a computer memory. These algorithmic descriptions and representations are the ways used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities. Usually, though not necessarily, these quantities take the form of electrical or magnetic signals capable of being stored, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. The disclosure can refer to the action and processes of a computer system, or similar electronic computing device, that manipulates and transforms data represented as physical (electronic) quantities within the computer system's registers and memories into other data similarly represented as physical quantities within the computer system memories or registers or other such information storage systems.

The disclosure also relates to an apparatus for performing the operations herein. This apparatus can be specially constructed for the intended purposes, or it can include a general purpose computer selectively activated or reconfigured by a computer program stored in the computer. Such a computer program can be stored in a computer readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, each coupled to a computer system bus.

The algorithms and displays presented herein are not inherently related to any particular computer or other apparatus. Various general purpose systems can be used with programs in accordance with the teachings herein, or it can prove convenient to construct a more specialized apparatus to perform the method. The structure for a variety of these systems will appear as set forth in the description below. In addition, the disclosure is not described with reference to any particular programming language. It will be appreciated that a variety of programming languages can be used to implement the teachings of the disclosure as described herein.

The disclosure can be provided as a computer program product, or software, that can include a machine-readable medium having stored thereon instructions, which can be used to program a computer system (or other electronic devices) to perform a process according to the disclosure. A machine-readable medium includes any mechanism for storing information in a form readable by a machine (e.g., a computer). In some implementations, a machine-readable (e.g., computer-readable) medium includes a machine (e.g., a computer) readable storage medium such as a read only memory ("ROM"), random access memory ("RAM"), magnetic disk storage media, optical storage media, flash memory devices, etc. The words "example" or "exemplary" are used herein to mean serving as an example, instance, or illustration. Any aspect or design described herein as "example" or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or." That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims may generally be construed to mean "one or more" unless specified otherwise or clear from context to be directed to a singular form. Moreover, use of the term "an embodiment" or "one embodiment" or "an implementation" or "one implementation" or the like throughout may or may not mean the same embodiment or implementation. One or more embodiments or implementations described herein may be combined in a particular embodiment or implementation. The terms "first," "second," "third," "fourth," etc. as used herein are meant as labels to distinguish among different elements and may not necessarily have an ordinal meaning according to their numerical designation.

In the foregoing specification, implementations of the disclosure have been described with reference to specific example implementations thereof. It will be evident that various modifications can be made thereto without departing from the broader spirit and scope of implementations of the disclosure as set forth in the following claims. The specification and drawings are, accordingly, to be regarded in an illustrative sense rather than a restrictive sense.

What is claimed is:

1. An intraoral scanner system comprising:
a probe with a sensing face;

a plurality of patterned light sources that are coupled to the probe, each of the plurality of patterned light sources configured to emit a pattern of light from a different location of a first plurality of locations with respect to the sensing face of the probe;

a plurality of un-patterned light sources coupled to the probe, each of the plurality of un-patterned light sources configured to emit un-patterned light from a different location of a second plurality of locations with respect to the sensing face of the probe;

a plurality of near infrared (NIR) light sources coupled to the probe, each of the plurality of NIR light sources configured to emit NIR light from a different location of a third plurality of locations with respect to the sensing face of the probe;

a plurality of cameras coupled to the probe, each of the plurality of cameras configured to receive one or more of returning patterned light, returning un-patterned light or returning NIR light reflected by a dental site; and one or more processing devices, the one or more processing devices configured to control an operation of the plurality of patterned light sources, the plurality of un-patterned light sources, and the plurality of NIR light sources, the one or more processing devices configured to alternately illuminate the dental site using a first NIR light source of the plurality of NIR light sources to generate a first image and a second NIR light source of the plurality of NIR light sources to generate a second image, and the one or more processing devices further configured to generate, based on the first image and the second image, a first blended NIR image that reduces saturated image areas of one or more of the first image or the second image.

2. The intraoral scanner system of claim 1, further comprising:
a plurality of polarizing filters coupled to the plurality of cameras, each of the plurality of polarizing filters having a first polarization axis.

3. The intraoral scanner system of claim 2, wherein each of the plurality of patterned light sources are configured to emit the pattern of light at a second polarization axis, wherein the first polarization axis is substantially parallel to the second polarization axis.

4. The intraoral scanner system of claim 3, wherein each of the plurality of NIR light sources are configured to emit the NIR light at a third polarization axis, wherein the first polarization axis is substantially perpendicular to the third polarization axis.

5. The intraoral scanner system of claim 1, wherein the one or more processing devices are configured to operate in an alternating mode to alternately illuminate the dental site by respective light sources within one or more of the plurality of patterned light sources, the plurality of un-patterned light sources, or the plurality of NIR light sources.

6. The intraoral scanner system of claim 5, wherein to operate in the alternating mode to alternately illuminate the dental site, the one or more processing devices to:
activate one or more first NIR light sources of the plurality of NIR light sources at a first instance in time to emit first NIR light from a first location of the third plurality of locations with respect to the sensing face of the probe and to provide a first illumination of the dental site;

generate first NIR scan data comprising a first NIR image of the dental site based on the first illumination;

activate one or more second NIR light sources of the plurality of NIR light sources at a second instance in time to emit second NIR light from a second location of the third plurality of locations with respect to the sensing face of the probe and to provide a second illumination of the dental site, wherein at least one of the one or more first NIR light sources are different than at least one of the one or more second NIR light sources; and generate second NIR scan data comprising a second NIR image of the dental site based on the second illumination.

7. The intraoral scanner system of claim 6, wherein the first instance in time and the second instance in time are sequential instances in time.

8. The intraoral scanner system of claim 6, the processing device further to:
generate a second blended NIR image of the dental site using the first NIR image and the second NIR image.

9. The intraoral scanner system of claim 8, the processing device further to:
perform an identification of a carious lesion at the dental site based on one or more of the first NIR image, the second NIR image, or the second blended NIR image.

10. The intraoral scanner system of claim 5, wherein the one or more processing devices are configured to operate in the alternating mode to alternately illuminate the dental site by respective light sources between two or more of the plurality of patterned light sources, the plurality of un-patterned light sources, or the plurality of NIR light sources.

11. An intraoral scanner system comprising:
a probe with a sensing face; and
one or more processing devices, to perform operations comprising:
emitting, at a first instance in time by a first light source of a probe of an intraoral scanner, first light at a first angle with respect to a dental site;
detecting, by a first camera of the probe, at least part of the first light reflected from the dental site;
emitting, at a second instance in time by a second light source of the probe, second light at a second angle with respect to the dental site;
detecting, by the first camera, at least part of the second light reflected from the dental site;
generating a first image of the dental site based on the detected first light and a second image of the dental site based on the detected second light; and
generating, using the first image and the second image, a blended image that reduces saturated image areas of one or more of the first image or the second image.

12. The intraoral scanner system of claim 11, wherein the first light source and the second light source are both from one of a plurality of patterned light sources configured to emit a pattern of light, a plurality of un-patterned light sources configured to emit un-patterned light, or a plurality of NIR light sources configured to emit NIR light.

13. The intraoral scanner system of claim 11, wherein the first light source and the second light source are from different ones of a plurality of patterned light sources configured to emit a pattern of light, a plurality of un-patterned light sources configured to emit un-patterned light, or a plurality of near infrared (NIR) light sources configured to emit NIR light.

14. The intraoral scanner system of claim 11, wherein the first instance in time and the second instance in time are sequential instances in time.

15. The intraoral scanner system of claim 11,
wherein detecting, by the first camera of the probe, the at least part of the first light reflected from the dental site comprises detecting the at least part of the first light reflected from the dental site that is filtered by a polarizing filter having a first polarization axis; and
wherein detecting, by the first camera, the at least part of the second light reflect from the dental site comprises detecting the at least part of the second light reflected from the dental site that is filtered by the polarizing filter having the first polarization axis.

16. The intraoral scanner system of claim 15, wherein each of the first light source and the second light source is a different one of a plurality of patterned light sources and is configured to emit a pattern of light at a second polarization axis, wherein the first polarization axis is substantially parallel to the second polarization axis.

17. The intraoral scanner system of claim 15, wherein each of the first light source and the second light source is a different one of a plurality of near infrared (NIR) light sources and is configured to emit NIR light at a third polarization axis, wherein the first polarization axis is substantially perpendicular to the third polarization axis.

18. The intraoral scanner system of claim 11, the operations further comprising:
generating a three-dimensional (3D) model of the dental site using one or more of the first image, the second image, or the blended image.

19. The intraoral scanner system of claim 18, wherein the first image is a first near infrared (NIR) image, the second image is a second NIR image and the blended image is a blended NIR image, the operations further comprising:
performing an identification of a carious lesion at the dental site based on the 3D model of the dental site.

* * * * *